(12) United States Patent
Tamashima

(10) Patent No.: US 9,309,191 B2
(45) Date of Patent: Apr. 12, 2016

(54) AMIDINE COMPOUND AND USE THEREOF

(71) Applicant: SUMITOMO CHEMICAL COMPANY, LIMITED, Tokyo (JP)

(72) Inventor: Hiroto Tamashima, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/779,095

(22) PCT Filed: Mar. 20, 2014

(86) PCT No.: PCT/JP2014/059054
§ 371 (c)(1),
(2) Date: Sep. 22, 2015

(87) PCT Pub. No.: WO2014/157596
PCT Pub. Date: Oct. 2, 2014

(65) Prior Publication Data
US 2016/0046564 A1 Feb. 18, 2016

(30) Foreign Application Priority Data

Mar. 25, 2013 (JP) .................................. 2013-061522

(51) Int. Cl.
*C07C 257/12* (2006.01)
*C07C 257/00* (2006.01)
*A01N 37/52* (2006.01)

(52) U.S. Cl.
CPC .............. *C07C 257/12* (2013.01); *A01N 37/52* (2013.01); *C07C 2101/02* (2013.01)

(58) Field of Classification Search
CPC ..... C07C 257/00; C07C 257/12; A01N 37/52
USPC .......................................... 514/637; 564/225
See application file for complete search history.

(56) References Cited

U.S. PATENT DOCUMENTS

| 4,149,874 | A | 4/1979 | Felix |
| 6,893,650 | B1 | 5/2005 | Charles et al. |
| 2005/0182025 | A1 | 8/2005 | Tseng |

FOREIGN PATENT DOCUMENTS

| GB | 2013669 A | 8/1979 |
| JP | 54-117431 A | 9/1979 |
| JP | 58-4757 A | 1/1983 |
| JP | 2002-536354 A | 10/2002 |
| JP | 2005-524706 A | 8/2005 |
| WO | WO 2012/090969 A1 | 7/2012 |

OTHER PUBLICATIONS

International Search Report, issued in PCT/JP2014/059054, dated Jun. 24, 2014.

*Primary Examiner* — Yevegeny Valenrod
(74) *Attorney, Agent, or Firm* — Birch, Stewart, Kolasch & Birch, LLP

(57) ABSTRACT

An amidine compound represented by formula (1)

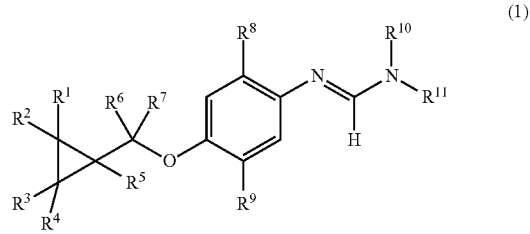

(1)

wherein $R^1$, $R^2$, $R^3$, $R^4$ and $R^5$ are the same or different and represent a C1 to C5 alkyl group optionally having one or more halogen atoms or the like; $R^6$ and $R^7$ are a hydrogen atom or the like; $R^8$ and $R^9$ are the same or different and represent a C1 to C3 alkyl group optionally having one or more halogen atoms or the like; and $R^{10}$ and $R^{11}$ are the same or different and represent a C1 to C6 alkyl group optionally having one or more halogen atoms or the like, has an excellent control effect on plant diseases.

5 Claims, No Drawings

AMIDINE COMPOUND AND USE THEREOF

TECHNICAL FIELD

The present invention relates to an amidine compound and use thereof.

BACKGROUND ART

Many compounds have been developed as an active ingredient of a plant disease controlling agent, and put to practical use (refer to WO2000/046184 A, WO2003/093224 A).

The present invention provides a compound having an excellent control effect on plant diseases.

DISCLOSURE OF THE INVENTION

As a result of an intensive study to find a compound having an excellent control effect on plant diseases, the present inventor has found that an amidine compound represented by the following formula (1) has an excellent control effect on plant diseases, and thereby reaching the present invention.

More specifically, the present invention includes the following invention.

[1] An amidine compound represented by formula (1)

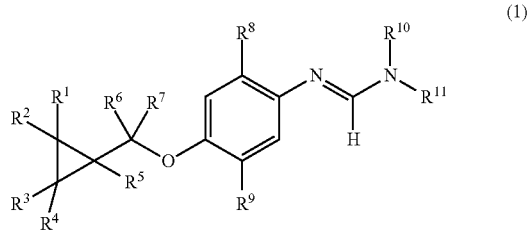

(1)

wherein
$R^1$, $R^2$, $R^3$, $R^4$ and $R^5$ each independently represent a C1 to C5 alkyl group optionally having one or more halogen atoms, a hydrogen atom, or a halogen atom;
$R^6$ and $R^7$ each independently represent a hydrogen atom or a C1 to C3 alkyl group optionally having one or more halogen atoms;
$R^8$ and $R^9$ each independently represent a C1 to C3 alkyl group optionally having one or more halogen atoms, a C1 to C2 alkoxy group optionally having one or more halogen atoms, or a halogen atom; and
$R^{10}$ and $R^{11}$ each independently represent a C1 to C6 alkyl group optionally having one or more halogen atoms or a C2 to C6 alkenyl group optionally having one or more halogen atoms
(hereinafter, may be referred to as Compound of Present Invention (1)).

[2] The amidine compound according to [1], wherein
$R^8$ and $R^9$ are each independently a methyl group optionally having one or more halogen atoms;
$R^{10}$ is a methyl group; and
$R^{11}$ is a C1 to C3 alkyl group or a C2 to C3 alkenyl group.

[3] The amidine compound according to [1], wherein
$R^1$, $R^2$, $R^3$, $R^4$ and $R^5$ are each independently a C1 to C5 alkyl group, a hydrogen atom or a halogen atom;
$R^8$, $R^9$ and $R^{10}$ are a methyl group; and
$R^{11}$ is an ethyl group, a propyl group or a 2-propenyl group.

[4] A plant disease controlling agent comprising the amidine compound as defined in any one of [1] to [3] (hereinafter, referred to as the controlling agent of the present invention).

[5] A method for controlling plant diseases comprising applying an effective amount of the amidine compound as defined in any one of [1] to [3] to a plant or soil.

[6] Use of the amidine compound as defined in any one of [1] to [3] for controlling plant diseases.

A plant disease can be controlled by using Compound of Present Invention (1).

MODE FOR CARRYING OUT THE INVENTION

Substituents in the present invention will be described below.

The halogen atom includes a fluorine atom, a chlorine atom, a bromine atom, and an iodine atom.

The C1 to C5 alkyl group represents a linear or branched alkyl group having 1 to 5 carbon atoms, and examples include a methyl group, an ethyl group, a propyl group, an isopropyl group, a butyl group, an isobutyl group, a tertiary butyl group, a pentyl group, a 2-methylbutyl group, and a 3-methylbutyl group.

The C1 to C5 alkyl group optionally having one or more halogen atoms represents a C1 to C5 alkyl group and a C1 to C5 haloalkyl group. The C1 to C5 haloalkyl group represents a group in which at least one hydrogen atom of the C1 to C5 alkyl group is substituted with a halogen atom, and examples include a monofluoromethyl group, a monochloromethyl group, a dichloromethyl group, a difluoromethyl group, a trifluoromethyl group, a trichloromethyl group, a tribromomethyl group, a chlorofluoromethyl group, a dichlorofluoromethyl group, a 2,2,2-trifluoroethyl group, a 2,2,2-trichloroethyl group, a pentafluoroethyl group, a chlorodifluoromethyl group, a 2,2-difluoroethyl group, a 2-chloro-2-fluoroethyl group, a 2-chloro-2,2-difluoroethyl group, a 2,2-dichloro-2-fluoroethyl group, a 2-fluoropropyl group, a 3-fluoropropyl group, a 2,2-difluoropropyl group, a 3,3,3-trifluoropropyl group, a 3-(fluoromethyl)-3-fluoropropyl group, a 4-fluorobutyl group, and a 5-fluoropentyl group. Examples of the halogen atom that can substitute for a hydrogen atom include a fluorine atom, a chlorine atom, a bromine atom, and an iodine atom.

The C1 to C3 alkyl group represents a linear or branched alkyl group and examples include a methyl group, an ethyl group, a propyl group, and an isopropyl group.

The C1 to C3 alkyl group optionally having one or more halogen atoms represents a C1 to C3 alkyl group and a C1 to C3 haloalkyl group. The C1 to C3 haloalkyl group represents a group in which at least one hydrogen atom of the C1 to C3 alkyl group is substituted with a halogen atom, and examples include a monofluoromethyl group, a monochloromethyl group, a dichloromethyl group, a difluoromethyl group, a trifluoromethyl group, a trichloromethyl group, a tribromomethyl group, a chlorofluoromethyl group, a dichlorofluoromethyl group, a 2,2,2-trifluoroethyl group, a 2,2,2-trichloroethyl group, a pentafluoroethyl group, a chlorodifluoromethyl group, a 2,2-difluoroethyl group, a 2-chloro-2-fluoroethyl group, a 2-chloro-2,2-difluoroethyl group, a 2,2-dichloro-2-fluoroethyl group, a 2-fluoropropyl group, a 3-fluoropropyl group, a 2,2-difluoropropyl group, and a 3,3,3-trifluoropropyl group. Examples of the halogen atom that can substitute for a hydrogen atom include a fluorine atom, a chlorine atom, a bromine atom, and an iodine atom.

The C1 to C6 alkyl group represents a linear or branched alkyl group having 1 to 6 carbon atoms, and examples include a methyl group, an ethyl group, a propyl group, an isopropyl group, a butyl group, an isobutyl group, a tertiary butyl group, a pentyl group, a 2-methylbutyl group, a 3-methylbutyl group, and a hexyl group.

The C1 to C6 alkyl group optionally having one or more halogen atoms represents a C1 to C6 alkyl group and a C1 to C6 haloalkyl group. The C1 to C6 haloalkyl group represents a group in which at least one hydrogen atom of the C1 to C6 alkyl group is substituted with a halogen atom, and examples include a monofluoromethyl group, a monochloromethyl group, a dichloromethyl group, a difluoromethyl group, a trifluoromethyl group, a trichloromethyl group, a tribromomethyl group, a chlorofluoromethyl group, a dichlorofluoromethyl group, a 2,2,2-trifluoroethyl group, a 2,2,2-trichloroethyl group, a pentafluoroethyl group, a chlorodifluoromethyl group, a 2,2-difluoroethyl group, a 2-chloro-2-fluoroethyl group, a 2-chloro-2,2-difluoroethyl group, a 2,2-dichloro-2-fluoroethyl group, a 2-fluoropropyl group, a 3-fluoropropyl group, a 2,2-difluoropropyl group, a 3,3,3-trifluoropropyl group, a 3-(fluoromethyl)-3-fluoropropyl group, a 4-fluorobutyl group, a 5-fluoropentyl group, and a 2,2-difluorohexyl group. Examples of the halogen atom that can substitute for a hydrogen atom include a fluorine atom, a chlorine atom, a bromine atom, and an iodine atom.

The C2 to C6 alkenyl group represents a linear or branched alkenyl group, and examples include a vinyl group, a 1-propenyl group, an isopropenyl group, a 2-propenyl group, a 1-butenyl group, a 1-methyl-1-propenyl group, a 2-butenyl group, a 1-methyl-2-propenyl group, a 3-butenyl group, a 2-methyl-1-propenyl group, a 2-methyl-2-propenyl group, a 1,3-butadienyl group, a 1-pentenyl group, a 1-ethyl-2-propenyl group, a 2-pentenyl group, a 1-methyl-1-butenyl group, a 3-pentenyl group, a 1-methyl-2-butenyl group, a 4-pentenyl group, a 1-methyl-3-butenyl group, a 3-methyl-1-butenyl group, a 1,2-dimethyl-2-propenyl group, a 1,1-dimethyl-2-propenyl group, a 2-methyl-2-butenyl group, a 3-methyl-2-butenyl group, a 1,2-dimethyl-1-propenyl group, a 2-methyl-3-butenyl group, a 3-methyl-3-butenyl group, a 1,3-pentadienyl group, a 1-vinyl-2-propenyl group, a 1-hexenyl group, and a 5-hexenyl group.

The C2 to C6 alkenyl group optionally having one or more halogen atoms represents a C2 to C6 alkenyl group and a C2 to C6 haloalkenyl group. The C2 to C6 haloalkenyl group represents a group in which at least one hydrogen atom of the C2 to C6 alkenyl group is substituted with a halogen atom, and examples include a 2-chlorovinyl group, a 2-bromovinyl group, an 2-iodovinyl group, a 3-chloro-2-propenyl group, a 3-bromo-2-propenyl group, a 1-chloromethylvinyl group, a 2-bromo-1-methylvinyl group, a 1-trifluoromethylvinyl group, a 3,3,3-trichloro-1-propenyl group, a 3-bromo-3,3-difluoro-1-propenyl group, a 2,3,3,3-tetrachloro-1-propenyl group, a 1-trifluoromethyl-2,2-difluorovinyl group, a 2-chloro-2-propenyl group, a 3,3-difluoro-2-propenyl group, a 2,3,3-trichloro-2-propenyl group, a 3,3-dichloro-2-propenyl group, a 3,3-dibromo-2-propenyl group, a 3-fluoro-3-chloro-2-propenyl group, a 4-bromo-3-chloro-3,4,4-trifluoro-1-butenyl group, a 1-bromomethyl-2-propenyl group, a 3-chloro-2-butenyl group, a 4,4,4-trifluoro-2-butenyl group, a 4-bromo-4,4-difluoro-2-butenyl group, a 3-bromo-3-butenyl group, a 3,4,4-trifluoro-3-butenyl group, a 3,4,4-tribromo-3-butenyl group, a 3-bromo-2-methyl-2-propenyl group, a 3,3-difluoro-2-methyl-2-propenyl group, a 3,3,3-trifluoro-2-methyl-1-propenyl group, a 3-chloro-4,4,4-trifluoro-2-butenyl group, a 3,3,3-trifluoro-1-methyl-1-propenyl group, a 3,4,4-trifluoro-1,3-butadienyl group, a perfluoro-1-butenyl group, a perfluoro-3-butenyl group, a 3,4-dibromo-1-pentenyl group, a 4,4-difluoro-3-methyl-3-butenyl group, a 3,3,4,4,5,5,5-heptafluoro-1-pentenyl group, a 5,5-difluoro-4-pentenyl group, a 4,5,5-trifluoro-4-pentenyl group, a 3,4,4,4-tetrafluoro-3-trifluoromethyl-1-butenyl group, a 4,4,4-trifluoro-3-methyl-2-butenyl group, a 3,5,5-trifluoro-2,4-pentadienyl group, a perfluoro-1-pentenyl group, a perfluoro-4-pentenyl group, a 4,4,5,5,6,6,6-heptafluoro-2-hexenyl group, a 3,4,4,5,5,5-hexafluoro-3-trifluoromethyl-1-pentenyl group, a 4,5,5,5-tetrafluoro-4-trifluoromethyl-2-pentenyl group, a 5-bromo-4,5,5-trifluoro-4-trifluoromethyl-2-pentenyl group, a perfluoro-1-hexenyl group, and a perfluoro-5-hexenyl group. Examples of the halogen atom that can substitute for a hydrogen atom include a fluorine atom, a chlorine atom, a bromine atom, and an iodine atom.

The C2 to C3 alkenyl group represents a linear or branched alkenyl group and examples include a vinyl group, a 1-propenyl group, and an isopropenyl group.

The methyl group optionally having one or more halogen atoms represents a group in which at least one hydrogen atom of the methyl group is substituted with a halogen atom, and examples include a monofluoromethyl group, a monochloromethyl group, a dichloromethyl group, a difluoromethyl group, a trifluoromethyl group, a trichloromethyl group, a tribromomethyl group, a chlorofluoromethyl group, and a dichlorofluoromethyl group. Examples of the halogen atom that can substitute for a hydrogen atom include a fluorine atom, a chlorine atom, a bromine atom, and an iodine atom.

The C1 to C2 alkoxy group represents a methoxy group and an ethoxy group. The C1 to C2 alkoxy group optionally having one or more halogen atoms represents a group in which at least one hydrogen atom of the methoxy group or ethoxy group is substituted with a halogen atom, and examples include a monofluoromethoxy group, a monochloromethoxy group, a monobromomethoxy group, a difluoromethoxy group, a dichloromethoxy group, a trifluoromethoxy group, a trichloromethoxy group, a 2-fluoroethoxy group, a 2,2,2-trifluoroethoxy group, a 2,2,2-trichloroethoxy group, a pentafluoroethoxy group, a 2,2-difluoroethoxy group, a 2-chloro-2-fluoroethoxy group, a 2-chloro-2,2-difluoroethoxy group, and a 2,2-dichloro-2-fluoroethoxy group. Examples of the halogen atom that can substitute for a hydrogen atom include a fluorine atom, a chlorine atom, a bromine atom, and an iodine atom.

Examples of the embodiments of Compound of Present Invention (1) include compounds having the substituent in the formula (1) as shown below.

Compounds wherein $R^1$ to $R^4$ are each independently a C1 to C5 alkyl group, a hydrogen atom or a halogen atom;

Compounds wherein $R^1$ to $R^4$ are each independently a methyl group or a hydrogen atom;

Compounds wherein $R^5$ is a C1 to C5 alkyl group or a hydrogen atom;

Compounds wherein $R^5$ is a methyl group or a hydrogen atom;

Compounds wherein $R^6$ is a hydrogen atom, and $R^7$ is a C1 to C3 alkyl group or a hydrogen atom;

Compounds wherein $R^6$ is a hydrogen atom, and $R^7$ is a methyl group or a hydrogen atom;

Compounds wherein $R^8$ and $R^9$ are a methyl group optionally having one or more halogen atoms;

Compounds wherein $R^8$ and $R^9$ are a methyl group;

Compounds wherein $R^8$ and $R^9$ are a trifluoromethyl group;

Compounds wherein $R^8$ and $R^9$ are a methoxy group;

Compounds wherein $R^8$ is a methyl group, and $R^9$ is a trifluoromethyl group;

Compounds wherein $R^8$ is a trifluoromethyl group, and $R^9$ is a methyl group;

Compounds wherein $R^{10}$ and $R^{11}$ are each independently a C1 to C6 alkyl group or a C2 to C6 alkenyl group;

Compounds wherein $R^{10}$ and $R^{11}$ are each independently a C1 to C3 alkyl group or a C2 to C3 alkenyl group;

Compounds wherein $R^{10}$ is a methyl group, and $R^{11}$ is an ethyl group, a propyl group or a propenyl group;

Compounds wherein $R^{10}$ is a methyl group, and $R^{11}$ is an ethyl group or a propyl group;

Compounds wherein $R^1$ to $R^5$ are each independently a C1 to C5 alkyl group, a hydrogen atom or a halogen atom, $R^8$ and $R^9$ are each independently a methyl group optionally having one or more halogen atoms, $R^{10}$ is a methyl group, and $R^{11}$ is a C1 to C3 alkyl group or a C2 to C3 alkenyl group;

Compounds wherein $R^1$ to $R^5$ are each independently a C1 to C5 alkyl group, a hydrogen atom or a halogen atom, $R^8$ to $R^{10}$ are a methyl group, and $R^{11}$ is an ethyl group or a propyl group;

Compounds wherein $R^1$ to $R^4$ are a hydrogen atom, $R^5$ is a methyl group, $R^6$ and $R^7$ are a hydrogen atom, $R^8$ and $R^9$ are each independently a methyl group optionally having one or more halogen atoms, $R^{10}$ is a methyl group, and $R^{11}$ is an ethyl group or a propyl group;

Compounds wherein $R^1$ to $R^4$ are a hydrogen atom, $R^5$ is a methyl group, $R^6$ and $R^7$ are a hydrogen atom, $R^8$ and $R^9$ are a methyl group, $R^{10}$ is a methyl group, and $R^{11}$ is an ethyl group or a propyl group;

Compounds wherein $R^1$, $R^2$, $R^3$, $R^4$ and $R^5$ are each independently a C1 to C5 alkyl group optionally having one or more halogen atoms, a hydrogen atom or a halogen atom, $R^6$ and $R^7$ are each independently a hydrogen atom or a C1 to C3 alkyl group, $R^8$ and $R^9$ are each independently a C1 to C3 alkyl group optionally having one or more halogen atoms, and $R^{10}$ and $R^{11}$ are each independently a C1 to C6 alkyl group optionally having one or more halogen atoms or a C2 to C6 alkenyl group optionally having one or more halogen atoms;

Compounds wherein $R^1$ and $R^2$ are each independently a C1 to C5 alkyl group optionally having one or more halogen atoms, a hydrogen atom or a halogen atom, $R^3$, $R^4$, $R^5$ and $R^6$ are each independently a C1 to C5 alkyl group optionally having one or more halogen atoms or a hydrogen atom, $R^7$ is a hydrogen atom, $R^8$, $R^9$ and $R^{10}$ are each independently a C1 to C3 alkyl group optionally having one or more halogen atoms, and $R^{11}$ is a C1 to C6 alkyl group optionally having one or more halogen atoms or a C2 to C6 alkenyl group optionally having one or more halogen atoms.

Compound of Present Invention (1) can be produced, for example, according to the following production method.

(Production Method 1)

Compound of Present Invention (1) can be produced by reacting a compound represented by the following formula (2) (hereinafter, may be referred to as compound (2)) with trimethyl orthoformate in the presence of an acid, and then reacting with a compound represented by the following formula (3) (hereinafter, may be referred to as compound (3)).

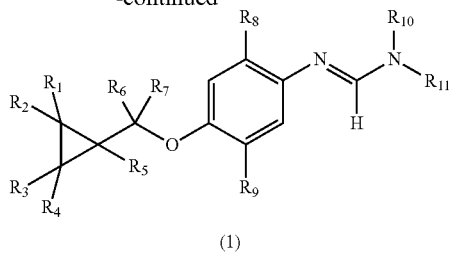

In the formula, $R^1$ to $R^{11}$ represent the same meaning as described above.

The reaction is usually carried out in a solvent.

Examples of the solvent used in the reaction include ethers such as tetrahydrofuran, ethylene glycol dimethyl ether and tertiary butyl methyl ether (hereinafter, referred to as MTBE), aromatic hydrocarbons such as toluene and xylene, halogenated hydrocarbons such as chlorobenzene, and mixtures thereof.

The acid used in the reaction includes p-toluenesulfonic acid, pyridinium p-toluenesulfonate, and the like.

In the reaction, the compound (3) is usually used in a ratio of 1 to 10 mol, and the acid is usually used in a ratio of 0.01 to 1 mol, based on 1 mol of the compound (2), and the amount of trimethyl orthoformate is usually a ratio of 1 to 100 grams, based on 1 gram of the compound (2). Trimethyl orthoformate can be also used as a solvent.

The reaction temperature in the reaction is usually in the range of −20 to 150° C. The reaction time in the reaction is usually in the range of 0.1 to 24 hours.

After completion of the reaction, the reaction mixture is subjected to post-treatment operations, for example, the reaction mixture is extracted with an organic solvent, and the organic layer is subjected to drying and concentration, whereby Compound of Present Invention (1) can be isolated. The isolated Compound of Present Invention (1) also can be further purified by chromatography, recrystallization, or the like.

Next, the method for synthesizing an intermediate compound will be described in detail.

(Reference Production Method 1)

The compound (2) can be produced by reducing a compound represented by the following formula (4) (hereinafter, may be referred to as compound (4)). Examples of the reduction reaction include a reaction with iron powder or tin in an aqueous acetic acid solution or an aqueous hydrochloric acid solution, and a catalytic reduction and the like. Preferred conditions include a reaction with iron powder in an aqueous acetic acid solution.

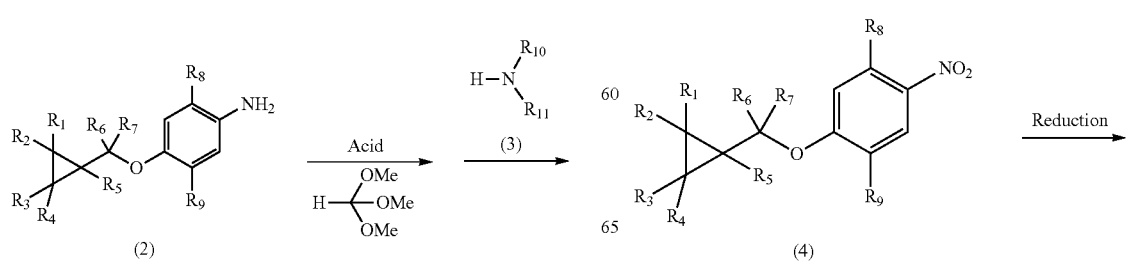

-continued

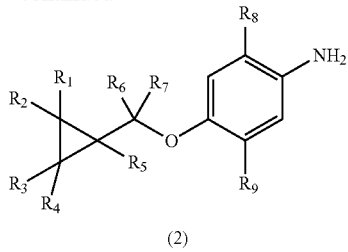

(2)

In the formula, $R^1$ to $R^8$ and $R^9$ represent the same meaning as described above.

The reaction is usually carried out in a solvent.

Examples of the solvent used in the reaction include water, a mixture of water and tetrahydrofuran, a mixture of water and ethanol, and the like.

In the reaction, iron powder is usually used in a ratio of 1 to 10 mol, based on 1 mol of the compound (4). The amount of acetic acid is usually a ratio of 1 to 100 grams, based on 1 gram of the compound (4). Acetic acid can be also used as a solvent.

The reaction temperature in the reaction is usually in the range of −20 to 150° C. The reaction time in the reaction is usually in the range of 0.1 to 24 hours.

After completion of the reaction, the reaction mixture is subjected to post-treatment operations, for example, the reaction mixture is extracted with an organic solvent, and the organic layer is subjected to drying and concentration, whereby the compound (2) can be isolated. The isolated compound (2) also can be further purified by chromatography, recrystallization, or the like.

(Reference Production Method 2)

The compound (4) can be produced by reacting a compound represented by the following formula (5) (hereinafter, may be referred to as compound (5)) with a compound represented by the following formula (6) (hereinafter, may be referred to as compound (6)) in the presence of triphenylphosphine and an azo compound.

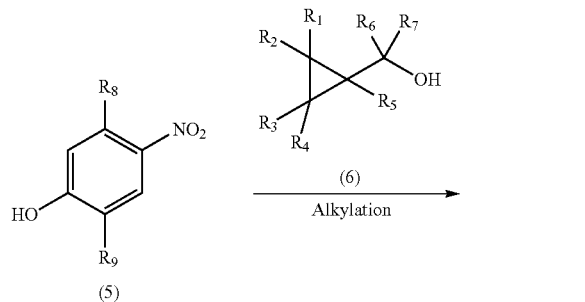

In the formula, $R^1$ to $R^9$ represent the same meaning as described above.

The reaction is usually carried out in a solvent.

Examples of the solvent used in the reaction include ethers such as tetrahydrofuran, ethylene glycol dimethyl ether and MTBE, aromatic hydrocarbons such as toluene and xylene, halogenated hydrocarbons such as chlorobenzene, and mixtures thereof.

Examples of the azo compound used in the reaction include bis(2-methoxyethyl) azodicarboxylate and diethyl azodicarboxylate.

In the reaction, the compound (6) is usually used in a ratio of 1 to 10 mol, triphenylphosphine is usually used in a ratio of 1 to 10 mol, and the azo compound is usually used in a ratio of 1 to 10 mol, based on 1 mol of the compound (5).

The reaction temperature in the reaction is usually in the range of −20 to 150° C. The reaction time in the reaction is usually in the range of 0.1 to 24 hours.

After completion of the reaction, the reaction mixture is subjected to post-treatment operations, for example, the reaction mixture is extracted with an organic solvent, and the organic layer is subjected to drying and concentration, whereby the compound (4) can be isolated. The isolated compound (4) also can be further purified by chromatography, recrystallization, or the like.

The controlling agent of the present invention may consist of only Compound of Present Invention (1), but is usually used by mixing Compound of Present Invention (1) with a solid carrier, a liquid carrier, a gaseous carrier, a surfactant or the like, and, if necessary, adding an auxiliary agent for formulation, such as a binder, a dispersant and a stabilizer as necessary, to be formulated into wettable powder, granular wettable powder, flowable, granules, dry flowable, emulsifiable concentrates, aqueous liquid formulation, oil solution, smoking pesticide, aerosol, microcapsules or the like. These formulations usually contain Compound of Present Invention (1) usually in an amount of 0.1 to 99% and preferably 0.2 to 90%, by weight ratio.

Examples of the solid carrier include fine powders or particles of followings: clays (e.g. kaolin, diatomaceous earth, synthetic hydrous silicon oxide, Fubasami clay, bentonite, acid clay), talcs, and other inorganic minerals (e.g. sericite, quartz powder, sulfur powder, activated carbon, calcium carbonate, hydrated silica). Examples of the liquid carrier include water, alcohols (e.g. methanol, ethanol), ketones (e.g. acetone, methyl ethyl ketone), aromatic hydrocarbons (e.g. benzene, toluene, xylene, ethylbenzene, methylnaphthalene), aliphatic hydrocarbons (e.g. n-hexane, cyclohexanone, kerosene), esters (e.g. ethyl acetate, butyl acetate), nitriles (e.g. acetonitrile, isobutyronitrile), ethers (e.g. dioxane, diisopropyl ether), acid amides (e.g. dimethylformamide, dimethylacetamide), halogenated hydrocarbons (e.g. dichloroethane, trichloroethylene, carbon tetrachloride), and the like.

Examples of the surfactant include alkylsulfate, alkyl sulfonates, alkylarylsulfonates, alkyl aryl ethers and polyoxyethylenated compounds thereof, polyoxyethylene glycol ethers, polyhydric alcohol esters, sugar alcohol derivatives, and the like.

Examples of other auxiliary agents for formulation include binders and dispersants, specifically, casein, gelatin, polysaccharides (e.g. starch, gum arabic, cellulose derivatives, alginic acid), lignin derivatives, bentonite, sugars, synthetic water-soluble polymers (e.g. polyvinyl alcohol, polyvinylpyrrolidone, polyacrylic acids), PAP (acidic isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, and fatty acids and esters thereof.

The method of applying the controlling agent of the present invention is not particularly limited, as far as the controlling agent of the present invention can be substantially applied, and examples thereof include treatment of a plant such as foliage spraying, treatment of a land such as soil treatment, treatment of a seed such as seed disinfection, and the like.

Also, the controlling agent of the present invention can be used in admixture with or simultaneously without mixing, with other fungicides, insecticides, acaricides, or nematicides.

Examples of other fungicides include those shown below.

(1) Azole Fungicides propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, flutriafol, simeconazole, ipconazole, and the like;

(2) Amine Fungicides fenpropimorph, tridemorph, fenpropidin, spiroxamine, and the like;

(3) Benzimidazole Fungicides carbendazim, benomyl, thiabendazole, thiophanate-Methyl, and the like;

(4) Dicarboximide Fungicides procymidone, iprodione, vinclozolin, and the like;

(5) Anilinopyrimidine Fungicides cyprodinil, pyrimethanil, mepanipyrim, and the like;

(6) Phenyl Pyrrole Fungicides fenpiclonil, fludioxonil, and the like;

(7) Strobilurin Fungicides kresoxim-methyl, azoxystrobin, trifloxystrobin, fluoxastrobin, picoxystrobin, pyraclostrobin, dimoxystrobin, pyribencarb, metominostrobin, orysastrobin, enestrobin, and the like;

(8) Phenylamide Fungicides metalaxyl, metalaxyl-M or mefenoxam, benalaxyl, benalaxyl-M or kiralaxyl, and the like;

(9) Carboxylic Acid Amide Fungicides dimethomorph, iprovalicarb, benthivalicarb-isopropyl, mandipropamid, valiphenal

(10) Carboxamide Fungicides carboxin, mepronil, flutolanil, thifluzamide, furametpyr, boscalid, penthiopyrad, fluopyram, bixafen, penflufen, sedaxane, fluxapyroxad, isopyrazam

(11) Other Fungicides diethofencarb; thiuram; fluazinam; mancozeb; chlorothalonil; captan; dichlofluanid; folpet; quinoxyfen; fenhexanid; fanoxadon; fenamidon; zoxamide; ethaboxam; amisulbrom; cyazofamid; metrafenone; cyflufenamid; proquinazid; flusulfamide; fluopicolide; fosetyl; cymoxanil; pencycuron; tolclofos-methyl; carpropamid; diclocymet; fenoxanil; tricyclazole; pyroquilon; probenazole; isotianil; tiadinil; tebufloquin; diclomezine; kasugamycin; ferimzone; fthalide; validamycin; hydroxyisoxazole; iminoctadine acetate; isoprothiolane; oxolinic acid; oxytetracycline; streptomycin; copper oxychloride; copper hydroxide; copper hydroxide sulfate; organocopper; sulfur; ametoctradin; fenpyrazamine, and an α-alkoxyphenylacetic acid compound represented by formula (12),

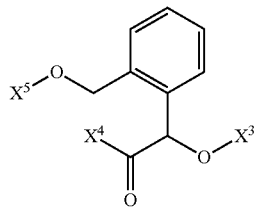

(12)

wherein $X^3$ represents a methyl group, a difluoromethyl group or an ethyl group, $X^4$ represents a methoxy group or a methylamino group, and $X^5$ represents a phenyl group, a 2-methylphenyl group or a 2,5-dimethylphenyl group.

Examples of other insecticides include those shown below.

(1) Organic Phosphorus Compounds acephate, aluminium phosphide, butathiofos, cadusafos, chlorethoxyfos, chlorfenvinphos, chlorpyrifos, chlorpyrifos-methyl, cyanophos:CYAP, diazinon, DCIP (dichlorodiisopropyl ether), dichlofenthion:ECP, dichlorvos:DDVP, dimethoate, dimethylvinphos, disulfoton, EPN, ethion, ethoprophos, etrimfos, fenthion:MPP, fenitrothion:MEP, fosthiazate, formothion, hydrogen phosphide, isofenphos, isoxathion, malathion, mesulfenfos, methidathion:DMTP, monocrotophos, naled:BRP, oxydeprofos:ESP, parathion, phosalone, phosmet:PMP, pirimiphos-methyl, pyridafenthion, quinalphos, phenthoate:PAP, profenofos, propaphos, prothiofos, pyraclorfos, salithion, sulprofos, tebupirimfos, temephos, tetrachlorvinphos, terbufos, thiometon, trichlorphon:DEP, vamidothion, phorate, cadusafos, and the like;

(2) Carbamate Compounds alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb:MIPC, metolcarb, methomyl, methiocarb, NAC, oxamyl, pirimicarb, propoxur:PHC, XMC, thiodicarb, xylylcarb, aldicarb, and the like;

(3) Synthetic Pyrethroid Compounds acrinathrin, allethrin, benfluthrin, beta-cyfluthrin, bifwentorin (bifenthrin), cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, furamethrin, tau-fluvalinate, 2,3,5,6-tetrafluoro-4-(methoxymethyl)benzyl(EZ)-(1RS,3RS; 1RS,3SR)-2,2-dimethyl-3-prop-1-enylcyclopropanecarboxylate, 2,3,5,6-tetrafluoro-4-methylbenzyl(EZ)-(1RS,3RS; 1RS,3SR)-2,2-dimethyl-3-prop-1-enylcyclopropanecarboxylate, 2,3,5,6-tetrafluoro-4-(methoxymethyl)benzyl(1RS,3RS; 1RS,3SR)-2,2-dimethyl-3-(2-methyl-1-propenyl)cyclopropanecarboxylate, and the like;

(4) Nereistoxin Compounds cartap, bensultap, thiocyclam, monosultap, bisultap, and the like;

(5) Neonicotinoid Compounds imidacloprid, nitenpyram, acetamiprid, thiamethoxam, thiacloprid, dinotefuran, clothianidin, and the like;

(6) Benzoyl Urea Compounds chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, triazuron, and the like;

(7) Phenylpyrazole Compounds
  acetoprole, ethiprole, fipronil, vaniliprole, pyriprole, pyrafluprole, and the like;
(8) Bt Toxin Insecticides
  Living spores derived from *Bacillus thuringiensis* and produced crystalline toxins and mixtures thereof;
(9) Hydrazine Compounds
  chromafenozide, halofenozide, methoxyfenozide, tebufenozide, and the like;
(10) Organic Chlorine Compounds
  aldrin, dieldrin, dienochlor, endosulfan, methoxychlor, and the like;
(11) Natural Insecticides
  machine oil, nicotine-sulfate;
(12) Other Insecticides
  avermectin-B, bromopropylate, buprofezin, chlorphenapyr, cyromazine, D-D(1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, nidinotefuran, potassium oleate, protrifenbute, spiromesifen, sulfur, metaflumizone, spirotetramat, pyrifluquinazone, spinetoram, chlorantraniliprole, cyantraniliprole, compounds represented by the following formula (K)

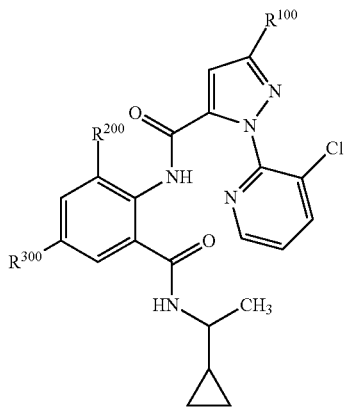

(K)

wherein
  $R^{100}$ represents chlorine, bromine or a trifluoromethyl group,
  $R^{200}$ represents chlorine, bromine or a methyl group, and
  $R^{300}$ represents chlorine, bromine or a cyano group,
  compounds represented by the following formula (L)

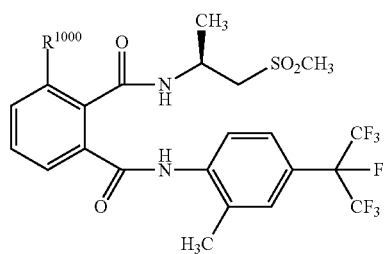

(L)

wherein
  $R^{1000}$ represents chlorine, bromine or iodine,
  and the like.
  Other acaricides (acaricidal active ingredients) include acequinocyl, amitraz, benzoximate, bifenaate, bromopropylate, chinomethionat, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite:BPPS, polynactins, pyridaben, pyrimidifen, tebufenpyrad, tetradifon, spirodiclofen, spiromesifen, spirotetramat, amidoflumet, cyenopyrafen, and the like.
  Examples of other nematicides (nematicidal active ingredients) include DCIP, fosthiazate, levamisol, methyisothiocyanate, morantel tartarate, imicyafos.
  While the application amount of the controlling agent of the present invention differs depending on weather conditions, formulation form, application period, application method, application place, subject disease, subject crop, and the like, and the amount of the compound of the present invention in the controlling agent of the present invention is usually 1 to 500 g, and preferably 2 to 200 g per 1000 $m^2$. An emulsifiable concentrate, wettable powder, suspension or the like is usually applied after diluting with water, and the concentration of Compound of Present Invention (1) in that case is usually 0.0005 to 2% by weight, and preferably 0.005 to 1% by weight, and dust, granules or the like is usually applied as it is without dilution. In the treatment of a seed, Compound of Present Invention (1) is applied in the range of usually 0.001 to 100 g, and preferably 0.01 to 50 g in the amount of the controlling agent of the present invention, relative to 1 Kg of seeds.
  The controlling agent of the present invention can be used as a plant disease controlling agent in agricultural lands such as cultivated lands, paddy fields, grass plot, and orchards. The controlling agent of the present invention can control diseases of agricultural lands, in agricultural lands where the "plants" and the like as follows are grown.
  Crops: corn, rice, wheat, barley, rye, oat, sorghum, cotton, soybean, peanut, sarrazin, sugar beet, rapeseed, sunflower, sugar cane, tobacco, etc., vegetables: solanaceae vegetables (eggplant, tomato, green pepper, hot pepper, potato, etc.), cucurbitaceae vegetables (cucumber, pumpkin, zucchini, watermelon, melon, etc.), cruciferae vegetables (Japanese radish, turnip, horseradish, kohlrabi, Chinese cabbage, cabbage, brown mustard, broccoli, cauliflower, etc.), compositae vegetables (burdock, garland *chrysanthemum*, artichoke, lettuce, etc.), liliaceae vegetables (Welsh onion, onion, garlic, asparagus, etc.), umbelliferae vegetables (carrot, parsley, celery, parsnip, etc.), chenopodiaceae vegetables (spinach, Swiss chard, etc.), labiatae vegetables (Japanese mint, mint, basil, etc.), strawberry, sweat potato, yam, aroid, etc., flowers, foliage plants,
  Fruit trees: pomaceous fruits (apple, common pear, Japanese pear, Chinese quince, quince, etc.), stone fleshy fruits (peach, plum, nectarine, Japanese plum, cherry, apricot, prune, etc.), citrus plants (Satsuma mandarin, orange, lemon, lime, grapefruits, etc.), nuts (chestnut, walnut, hazel nut, almond, pistachio, cashew nut, macadamia nut, etc.), berry fruits (blueberry, cranberry, blackberry, raspberry, etc.), grape, persimmon, olive, loquat, banana, coffee, date, coconut, etc.,
  Trees other than fruit trees: tea, mulberry, flowering trees and shrubs, street trees (ash tree, birch, dogwood, *eucalyptus*, ginkgo, lilac, maple tree, oak, poplar, *cercis*, Chinese sweet gum, plane tree, *zelkova*, Japanese arborvitae, fir tree, Japanese hemlock, needle juniper, pine, spruce, yew), etc.
  The "plants" also contain genetically modified plants.

Rice: *Magnaporthe grisea, Cochliobolus miyabeanus, Rhizoctonia solani, Gibberella fujikuroi*, and *Sclerophthora macrospora*; Wheat: *Erysiphe graminis, Fusarium graminearum, F. avenaceum, F. culmorum, Microdochium nivale, Puccinia striiformis, P. graminis, P. recondita, Micronectriella nivale, Typhula* sp., *Ustilago tritici, Tilletia caries, Pseudocercosporella herpotrichoides, Septoria tritici, Stagonospora nodorum*, and *Pyrenophora tritici-repentis*; Barley: *Erysiphe graminis, Fusarium graminearum, F. avenaceum, F. culmorum, Microdochium nivale, Puccinia striiformis, P. graminis, P. hordei, Ustilago nuda, Rhynchosporium secalis, Pyrenophora teres, Cochliobolus sativus, Pyrenophora graminea*, and *Rhizoctonia solani*; Family of wheat, barley and the like: *Erysiphe graminis, Fusarium graminearum, F. avenaceum, F. culmorum, Microdochium nivale, Puccinia striiformis, P. graminis, P. recondita, P. hordei, Typhula* sp., *Micronectriella nivalis, Ustilago tritici, U. nuda, Tilletia caries, Pseudocercosporella herpotrichoides, Rhynchosporium secalis, Septoria tritici, Leptosphaeria nodorum, Pyrenophora teres Drechsler, Gaeumannomyces graminis*, and *Pyrenophora tritici-repentis*; Citrus: *Diaporthe citri, Elsinoe fawcetti*, and *Penicillium digitatum, P. italicum*; Apple: *Monilinia mali, Valsa ceratosperma, Podosphaera leucotricha, Alternaria alternata* apple pathotype, *Venturia inaequalis*, and *Glomerella cingulata*; Pear: *Venturia nashicola, V. pirina, Alternaria alternata* Japanese pear pathotype, and *Gymnosporangium haraeanum*; Peach: *Monilinia fructicola, Cladosporium carpophilum*, and *Phomopsis* sp.; Grape: *Elsinoe ampelina, Glomerella cingulata, Uncinula necator, Phakopsora ampelopsidis, Guignardia bidwellii*, and *Plasmopara viticola*; Japanese persimmon: *Gloeosporium kaki*, and *Cercospora kaki, Mycosphaerella nawae*; Gourd: *Colletotrichum lagenarium, Sphaerotheca fuliginea, Mycosphaerella melonis, Fusarium oxysporum, Pseudoperonospora cubensis, Phytophthora* sp., and *Pythium* sp.; Tomato: *Alternaria solani, Cladosporium fulvum*, and *Phytophthora infestans*; Eggplant: *Phomopsis vexans*, and *Erysiphe cichoracearum*; Cruciferous vegetables: *Alternaria japonica, Cercosporella brassicae, Plasmodiophora parasitica*, and *Peronospora parasitica*; Welsh onion: *Puccinia allii*; Soybean: *Cercospora kikuchii, Elsinoe glycines, Diaporthe phaseolorum* var. *sojae*, and *Phakopsora pachyrhizi*; Kidney bean: *Colletotrichum lindemthianum*; Peanut: *Cercospora personata, Cercospora arachidicola* and *Sclerotium rolfsii*; Garden pea: *Erysiphe pisi*; Potato: *Alternaria solani, Phytophthora infestans*, and *Verticillium alboatrum, V. dahliae, V. nigrescens*; Strawberry: *Sphaerotheca humuli*; Tea: *Exobasidium reticulatum, Elsinoe leucospila, Pestalotiopsis* sp., and *Colletotrichum theae-sinensis*; Tobacco: *Alternaria longipes, Erysiphe cichoracearum, Colletotrichum tabacum, Peronospora tabacina*, and *Phytophthora nicotianae*; Sugar beet: *Cercospora beticola, Thanatephorus cucumeris, Thanatephorus cucumeris*, and *Aphanomyces sochlioides*; Rose: *Diplocarpon rosae*, and *Sphaerotheca pannosa*; Chrysanthemum: *Septoria chrysanthemi-indici*, and *Puccinia horiana*; Onion: *Botrytis cinerea, B. byssoidea, B. squamosa, Botrytis alli*, and *Botrytis squamosa*; Various crops: *Botrytis cinerea*, and *Sclerotinia sclerotiorum*; Japanese radish: *Alternaria brassicicola*; Turfgrass: *Sclerotinia homeocarpa*, and *Rhizoctonia solani*; and Banana: *Mycosphaerella fijiensis, Mycosphaerella musicola*.

EXAMPLES

Next, the present invention will be further specifically described by examples such as production examples, formulation examples, test examples, and the like. However, the present invention is not limited to these examples.

First, production examples will be shown.

Production Example 1

A mixture of 0.47 g of 2,5-dimethyl-4-[(1-methylcyclopropyl)methoxy]phenylamine, 0.04 g of p-toluenesulfonic acid monohydrate and 5 mL of trimethyl orthoformate was stirred under heating and refluxing for 1 hour. The cooled reaction mixture was concentrated under reduced pressure. The resulting residue and 5 mL of 1,4-dioxane were mixed at room temperature, and 0.5 mL of ethylmethylamine was added to the resulting mixture at room temperature. The resulting mixture was stirred at 80° C. for 2 hours. The reaction mixture was cooled to around room temperature, and then concentrated under reduced pressure. The resulting residue was subjected to silica gel column chromatography to obtain 0.15 g of N'-{2,5-dimethyl-4-[(1-methylcyclopropyl)methoxy]phenyl}-N-ethyl-N-methylformamidine (Compound of Present Invention (1-1)).

Compound of Present Invention (1-1)

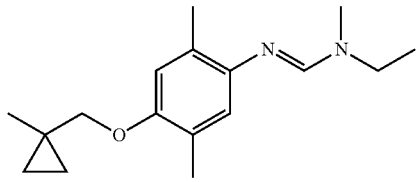 [SMILES: CCN(C)/C=N/c1cc(C)c(OCC2(C)CC2)cc1C]

$^1$H-NMR (CDCl$_3$) δ: 7.38 (1H, s), 6.58 (1H, s), 6.54 (1H, s), 3.68 (2H, s), 3.42-3.26 (2H, br m), 2.96 (3H, s), 2.21 (3H, s), 2.19 (3H, s), 1.23 (3H, s), 1.18 (3H, t, J=7.2 Hz), 0.54 (2H, dd, J=5.6, 4.4 Hz), 0.38 (2H, dd, J=5.9, 4.2 Hz).

Production Example 2

A mixture of 0.78 g of 2,5-dimethyl-4-[(1-methylcyclopropyl)methoxy]phenylamine, 0.12 g of p-toluenesulfonic acid monohydrate and 20 mL of trimethyl orthoformate was stirred under heating and refluxing for 2 hours. A saturated aqueous sodium bicarbonate solution was added to the cooled reaction mixture, and the mixture was extracted with ethyl acetate. The organic layer was washed with water and saturated salt water, dried over anhydrous magnesium sulfate, and then concentrated under reduced pressure. 0.26 g of the resulting residue and 10 mL of 1,4-dioxane were mixed at room temperature, and 0.5 mL of methylpropylamine was added to the resulting mixture at room temperature. The resulting mixture was stirred at 80° C. for 1 hour. The reaction mixture was cooled to around room temperature, and then concentrated under reduced pressure. The resulting residue was subjected to silica gel column chromatography to obtain 0.15 g of N'-{2,5-dimethyl-4-[(1-methylcyclopropyl)methoxy]phenyl}-N-methyl-N-propylformamidine (Compound of Present Invention (1-2)).

Compound of Present Invention (1-2)

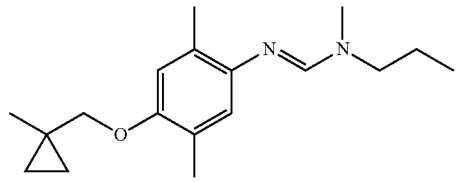 [SMILES: CCCN(C)/C=N/c1cc(C)c(OCC2(C)CC2)cc1C]

$^1$H-NMR (CDCl$_3$) δ: 7.39 (1H, s), 6.58 (1H, s), 6.54 (1H, s), 3.68 (2H, s), 3.37-3.07 (2H, br m), 2.97 (3H, s), 2.21 (3H, s), 2.19 (3H, s), 1.61 (2H, dd, J=14.3, 7.2 Hz), 1.23 (3H, s), 0.91 (3H, t, J=7.3 Hz), 0.54 (2H, t, J=5.0 Hz), 0.38 (2H, t, J=5.1 Hz).

Production Example 3

A mixture of 0.78 g of 2,5-dimethyl-4-[(1-methylcyclopropyl)methoxy]phenylamine, 0.12 g of p-toluenesulfonic acid monohydrate and 20 mL of trimethyl orthoformate was stirred under heating and refluxing for 2 hours. A saturated aqueous sodium bicarbonate solution was added to the cooled reaction mixture, and the mixture was extracted with ethyl acetate. The organic layer was washed with water and saturated salt water, dried over anhydrous magnesium sulfate, and then concentrated under reduced pressure. 0.25 g of the resulting residue and 10 mL of 1,4-dioxane were mixed at room temperature, and 0.5 mL of butylmethylamine was added to the resulting mixture at room temperature. The resulting mixture was stirred at 80° C. for 15 minutes. The reaction mixture was cooled to around room temperature, and then concentrated under reduced pressure. The resulting residue was subjected to silica gel column chromatography to obtain 0.17 g of N-butyl-N'-{2,5-dimethyl-4-[(1-methylcyclopropyl)methoxy]phenyl}-N-methylformamidine (Compound of Present Invention (1-3)).

Compound of Present Invention (1-3)

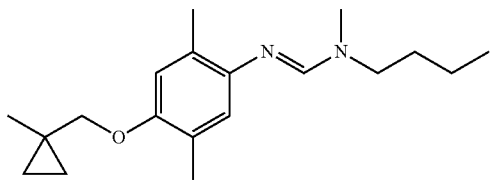 [SMILES: CCCCN(C)/C=N/c1cc(C)c(OCC2(C)CC2)cc1C]

$^1$H-NMR (CDCl$_3$) δ: 7.38 (1H, s), 6.58 (1H, s), 6.53 (1H, s), 3.68 (2H, s), 3.37-3.15 (2H, br m), 2.96 (3H, s), 2.21 (3H, s), 2.19 (3H, s), 1.61-1.52 (2H, m), 1.39-1.26 (2H, m), 1.23 (3H, s), 0.95 (3H, t, J=7.3 Hz), 0.54 (2H, t, J=5.0 Hz), 0.38 (2H, t, J=5.0 Hz).

Production Example 4

A mixture of 0.78 g of 2,5-dimethyl-4-[(1-methylcyclopropyl)methoxy]phenylamine, 0.12 g of p-toluenesulfonic acid monohydrate and 20 mL of trimethyl orthoformate was stirred under heating and refluxing for 2 hours. A saturated aqueous sodium bicarbonate solution was added to the cooled reaction mixture, and the mixture was extracted with ethyl acetate. The organic layer was washed with water and saturated salt water, dried over anhydrous magnesium sulfate, and then concentrated under reduced pressure. 0.21 g of the resulting residue and 10 mL of 1,4-dioxane were mixed at room temperature, and 0.5 mL of methylpentylamine was added to the resulting mixture at room temperature. The resulting mixture was stirred at 80° C. for 1 hour. The reaction mixture was cooled to around room temperature, and then concentrated under reduced pressure. The resulting residue was subjected to silica gel column chromatography to obtain 0.14 g of N'-{2,5-dimethyl-4-[(1-methylcyclopropyl)methoxy]phenyl}-N-methyl-N-pentylformamidine (Compound of Present Invention (1-4)).

Compound of Present Invention (1-4)

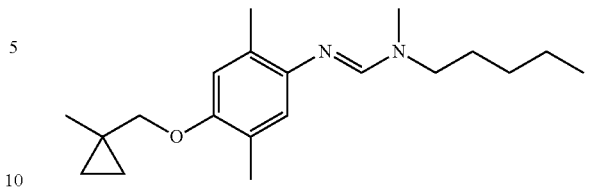

$^1$H-NMR (CDCl$_3$) δ: 7.38 (1H, s), 6.58 (1H, s), 6.54 (1H, s), 3.68 (2H, s), 3.38-3.12 (2H, br m), 2.96 (3H, s), 2.21 (3H, s), 2.19 (3H, s), 1.63-1.53 (2H, m), 1.40-1.25 (4H, m), 1.23 (3H, s), 0.91 (3H, t, J=7.1 Hz), 0.54 (2H, t, J=4.9 Hz), 0.38 (2H, t, J=5.1 Hz).

Production Example 5

A mixture of 0.78 g of 2,5-dimethyl-4-[(1-methylcyclopropyl)methoxy]phenylamine, 0.12 g of p-toluenesulfonic acid monohydrate and 20 mL of trimethyl orthoformate was stirred under heating and refluxing for 2 hours. A saturated aqueous sodium bicarbonate solution was added to the cooled reaction mixture, and the mixture was extracted with ethyl acetate. The organic layer was washed with water and saturated salt water, dried over anhydrous magnesium sulfate, and then concentrated under reduced pressure. 0.27 g of the resulting residue and 10 mL of 1,4-dioxane were mixed at room temperature, and 0.5 mL of allylmethylamine was added to the resulting mixture at room temperature. The resulting mixture was stirred at 80° C. for 1 hour. The reaction mixture was cooled to around room temperature, and then concentrated under reduced pressure. The resulting residue was subjected to silica gel column chromatography to obtain 0.20 g of N'-{2,5-dimethyl-4-[(1-methylcyclopropyl)methoxy]phenyl}-N-methyl-N-(2-propenyl)formamidine (Compound of Present Invention (1-5)).

Compound of Present Invention (1-5)

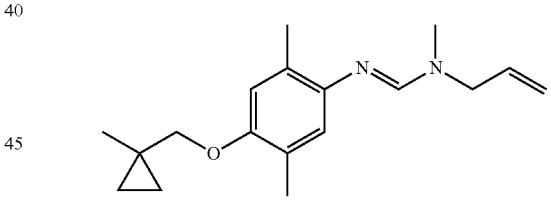

$^1$H-NMR (CDCl$_3$) δ: 7.42 (1H, s), 6.59 (1H, s), 6.55 (1H, s), 5.84 (1H, ddd, J=22.1, 5.5, 2.7 Hz), 5.25-5.17 (2H, m), 4.00-3.79 (2H, br m), 3.68 (2H, s), 2.95 (3H, s), 2.22 (3H, s), 2.20 (3H, s), 1.24 (3H, s), 0.54 (2H, t, J=4.9 Hz), 0.39 (2H, t, J=5.0 Hz).

Production Example 6

A mixture of 0.23 g of 4-cyclopropylmethoxy-2,5-dimethylphenylamine, 0.02 g of p-toluenesulfonic acid monohydrate and 10 mL of trimethyl orthoformate was stirred under heating and refluxing for 2 hours. The cooled reaction mixture was concentrated under reduced pressure. The resulting residue and 10 mL of 1,4-dioxane were mixed at room temperature, and 0.5 mL of ethylmethylamine was added to the resulting mixture at room temperature. The resulting mixture was stirred at 80° C. for 2 hours. The reaction mixture was cooled to around room temperature, and then concentrated under reduced pressure. The resulting residue was subjected to silica gel column chromatography to obtain 0.10 g of N'-(4-cyclopropylmethoxy-2,5-dimethylphenyl)-N-ethyl-N-methylformamidine (Compound of Present Invention (1-6)).

Compound of Present Invention (1-6)

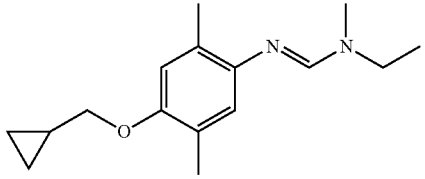 [SMILES: CCN(C)/C=N/c1cc(C)c(OCC2CC2)cc1C]

¹H-NMR (CDCl₃) δ: 7.38 (1H, s), 6.62 (1H, s), 6.54 (1H, s), 3.76 (2H, d, J=6.8 Hz), 3.42-3.24 (2H, br m), 2.97 (3H, s), 2.21 (3H, s), 2.19 (3H, s), 1.29-1.22 (1H, m), 1.19 (3H, t, J=7.2 Hz), 0.62-0.55 (2H, m), 0.35-0.30 (2H, m).

Production Example 7

A mixture of 0.23 g of 4-cyclopropylmethoxy-2,5-dimethylphenylamine, 0.02 g of p-toluenesulfonic acid monohydrate and 10 mL of trimethyl orthoformate was stirred under heating and refluxing for 2 hours. The cooled reaction mixture was concentrated under reduced pressure. The resulting residue and 10 mL of 1,4-dioxane were mixed at room temperature, and 0.5 mL of methylpropylamine was added to the resulting mixture at room temperature. The resulting mixture was stirred at 80° C. for 2 hours. The reaction mixture was cooled to around room temperature, and then concentrated under reduced pressure. The resulting residue was subjected to silica gel column chromatography to obtain 0.16 g of N'-(4-cyclopropylmethoxy-2,5-dimethylphenyl)-N-methyl-N-propylformamidine (Compound of Present Invention (1-7)).

Compound of Present Invention (1-7)

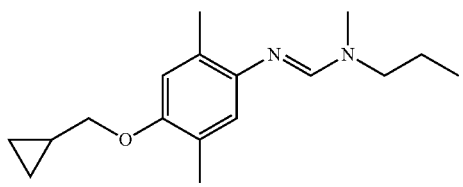 [SMILES: CCCN(C)/C=N/c1cc(C)c(OCC2CC2)cc1C]

¹H-NMR (CDCl₃) δ: 7.39 (1H, s), 6.63 (1H, s), 6.54 (1H, s), 3.76 (2H, d, J=6.8 Hz), 3.34-3.10 (2H, br m), 2.97 (3H, s), 2.21 (3H, s), 2.19 (3H, s), 1.67-1.56 (2H, m), 1.30-1.19 (1H, m), 0.91 (3H, t, J=7.4 Hz), 0.62-0.55 (2H, m), 0.35-0.30 (2H, m).

Production Example 8

A mixture of 0.23 g of 2,5-dimethyl-4-[(2-methylcyclopropyl)methoxy]phenylamine, 0.03 g of p-toluenesulfonic acid monohydrate and 10 mL of trimethyl orthoformate was stirred under heating and refluxing for 2 hours. The cooled reaction mixture was concentrated under reduced pressure. The resulting residue and 10 mL of 1,4-dioxane were mixed at room temperature, and 0.5 mL of ethylmethylamine was added to the resulting mixture at room temperature. The resulting mixture was stirred at 80° C. for 2 hours. The reaction mixture was cooled to around room temperature, and then concentrated under reduced pressure. The resulting residue was subjected to silica gel column chromatography to obtain 0.11 g of N'-{2,5-dimethyl-4-[(2-methylcyclopropyl)methoxy]phenyl}-N-ethyl-N-methylformamidine (Compound of Present Invention (1-8)).

Compound of Present Invention (1-8)

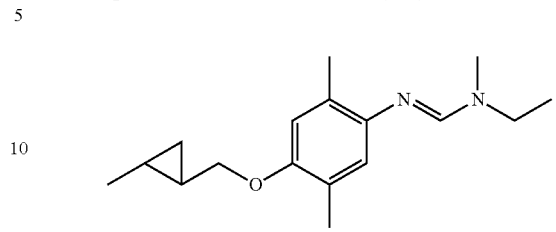

¹H-NMR (CDCl₃) δ: 7.38 (1H, s), 6.62 (1H, s), 6.54 (1H, s), 3.76 (2H, dd, J=6.6, 4.5 Hz), 3.42-3.27 (2H, br m), 2.97 (3H, s), 2.21 (3H, s), 2.18 (3H, s), 1.19 (3H, t, J=7.1 Hz), 1.07 (3H, d, J=6.0 Hz), 0.99-0.90 (1H, m), 0.78-0.68 (1H, m), 0.52-0.44 (1H, m), 0.38-0.28 (1H, m).

Production Example 9

A mixture of 0.25 g of 2,5-dimethyl-4-[(2-methylcyclopropyl)methoxy]phenylamine, 0.03 g of p-toluenesulfonic acid monohydrate and 10 mL of trimethyl orthoformate was stirred under heating and refluxing for 2 hours. The cooled reaction mixture was concentrated under reduced pressure. The resulting residue and 10 mL of 1,4-dioxane were mixed at room temperature, and 0.5 mL of methylpropylamine was added to the resulting mixture at room temperature. The resulting mixture was stirred at 80° C. for 2 hours. The reaction mixture was cooled to around room temperature, and then concentrated under reduced pressure. The resulting residue was subjected to silica gel column chromatography to obtain 0.13 g of N'-{2,5-dimethyl-4-[(2-methylcyclopropyl)methoxy]phenyl}-N-methyl-N-propylformamidine (Compound of Present Invention (1-9)).

Compound of Present Invention (1-9)

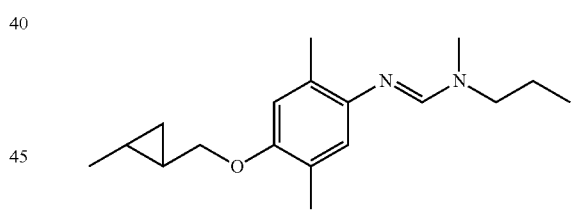

¹H-NMR (CDCl₃) δ: 7.39 (1H, s), 6.62 (1H, s), 6.53 (1H, s), 3.76 (2H, dd, J=6.8, 4.4 Hz), 3.29-3.15 (2H, br m), 2.97 (3H, s), 2.21 (3H, s), 2.18 (3H, s), 1.67-1.56 (2H, m), 1.07 (3H, d, J=5.8 Hz), 0.97-0.89 (1H, m), 0.91 (3H, t, J=7.4 Hz), 0.77-0.68 (1H, m), 0.51-0.44 (1H, m), 0.35-0.29 (1H, m).

Production Example 10

A mixture of 0.23 g of 4-(1-cyclopropylethoxy)-2,5-dimethylphenylamine, 0.03 g of p-toluenesulfonic acid monohydrate and 10 mL of trimethyl orthoformate was stirred under heating and refluxing for 2 hours. The cooled reaction mixture was concentrated under reduced pressure. The resulting residue and 10 mL of 1,4-dioxane were mixed at room temperature, and 0.5 mL of ethylmethylamine was added to the resulting mixture at room temperature. The resulting mixture was stirred at 80° C. for 2 hours. The reaction mixture was cooled to around room temperature, and then concentrated under reduced pressure. The resulting residue was subjected to silica gel column chromatography to obtain 0.12 g of N'-[4-(1-cyclopropylethoxy)-2,5-dimethylphenyl]-N-ethyl-N-methylformamidine (Compound of Present Invention (1-10)).

Compound of Present Invention (1-10)

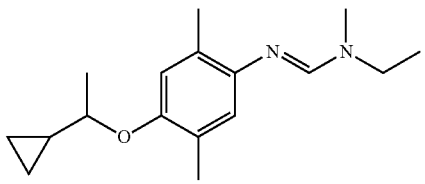 [SMILES: CCN(C)/C=N/c1cc(C)c(OC(C)C2CC2)cc1C]

¹H-NMR (CDCl₃) δ: 7.4 0 (1H, s), 6.65 (1H, s), 6.52 (1H, s), 3.68-3.60 (1H, m), 3.41-3.25 (2H, br m), 2.97 (3H, s), 2.20 (3H, s), 2.17 (3H, s), 1.33 (3H, d, J=6.2 Hz), 1.19 (3H, t, J=7.1 Hz), 1.13-1.02 (1H, m), 0.55-0.43 (2H, m), 0.37-0.30 (1H, m), 0.24-0.18 (1H, m).

Production Example 11

A mixture of 0.25 g of 4-(1-cyclopropylethoxy)-2,5-dimethylphenylamine, 0.02 g of p-toluenesulfonic acid monohydrate and 10 mL of trimethyl orthoformate was stirred under heating and refluxing for 2 hours. The cooled reaction mixture was concentrated under reduced pressure. The resulting residue and 10 mL of 1,4-dioxane were mixed at room temperature, and 0.5 mL of methylpropylamine was added to the resulting mixture at room temperature. The resulting mixture was stirred at 80° C. for 2 hours. The reaction mixture was cooled to around room temperature, and then concentrated under reduced pressure. The resulting residue was subjected to silica gel column chromatography to obtain 0.12 g of N'-[4-(1-cyclopropylethoxy)-2,5-dimethylphenyl]-N-methyl-N-propylformamidine (Compound of Present Invention (1-11)).

Compound of Present Invention (1-11)

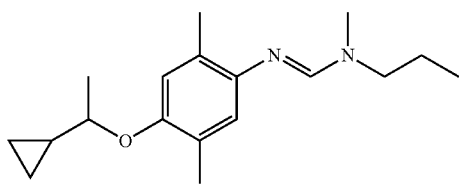 [SMILES: CCCN(C)/C=N/c1cc(C)c(OC(C)C2CC2)cc1C]

¹H-NMR (CDCl₃) δ: 7.40 (1H, s), 6.65 (1H, s), 6.52 (1H, s), 3.68-3.60 (1H, m), 3.31-3.13 (2H, br m), 2.97 (3H, s), 2.20 (3H, s), 2.17 (3H, s), 1.65-1.55 (2H, m), 1.33 (3H, d, J=6.0 Hz), 1.13-1.02 (1H, m), 0.91 (3H, t, J=7.4 Hz), 0.54-0.43 (2H, m), 0.37-0.30 (1H, m), 0.25-0.18 (1H, m).

Production Example 12

A mixture of 0.33 g of 2,5-dimethyl-4-[(2-propylcyclopropyl)methoxy]phenylamine, 0.03 g of p-toluenesulfonic acid monohydrate and 10 mL of trimethyl orthoformate was stirred under heating and refluxing for 2 hours. The cooled reaction mixture was concentrated under reduced pressure. The resulting residue and 10 mL of 1,4-dioxane were mixed at room temperature, and 0.5 mL of ethylmethylamine was added to the resulting mixture at room temperature. The resulting mixture was stirred at 80° C. for 2 hours. The reaction mixture was cooled to around room temperature, and then concentrated under reduced pressure. The resulting residue was subjected to silica gel column chromatography to obtain 0.19 g of N'-{2,5-dimethyl-4-[(2-propylcyclopropyl)methoxy]phenyl}-N-ethyl-N-methylformamidine (Compound of Present Invention (1-12)).

Compound of Present Invention (1-12)

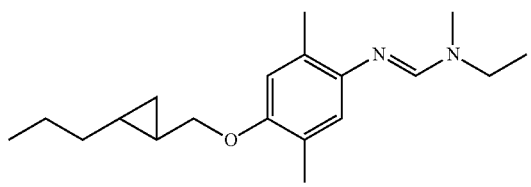 [SMILES: CCCC1CC1COc1cc(C)c(/N=C/N(C)CC)cc1C]

¹H-NMR (CDCl₃) δ: 7.38 (1H, s), 6.60 (1H, s), 6.54 (1H, s), 3.76 (2H, ddd, J=62.8, 9.9, 6.8 Hz), 3.42-3.25 (2H, br m), 2.97 (3H, s), 2.21 (3H, s), 2.18 (3H, s), 1.49-1.38 (2H, m), 1.38-1.28 (1H, m), 1.20-1.11 (1H, m), 1.19 (3H, t, J=7.1 Hz), 1.00-0.92 (1H, m), 0.93 (3H, t, J=7.3 Hz), 0.75-0.66 (1H, m), 0.50-0.44 (1H, m), 0.39-0.33 (1H, m).

Production Example 13

A mixture of 0.32 g of 2,5-dimethyl-4-[(2-propylcyclopropyl)methoxy]phenylamine, 0.03 g of p-toluenesulfonic acid monohydrate and 10 mL of trimethyl orthoformate was stirred under heating and refluxing for 2 hours. The cooled reaction mixture was concentrated under reduced pressure. The resulting residue and 10 mL of 1,4-dioxane were mixed at room temperature, and 0.5 mL of methylpropylamine was added to the resulting mixture at room temperature. The resulting mixture was stirred at 80° C. for 2 hours. The reaction mixture was cooled to around room temperature, and then concentrated under reduced pressure. The resulting residue was subjected to silica gel column chromatography to obtain 0.23 g of N'-{2,5-dimethyl-4-[(2-propylcyclopropyl)methoxy]phenyl}-N-methyl-N-propylformamidine (Compound of Present Invention (1-13)).

Compound of Present Invention (1-13)

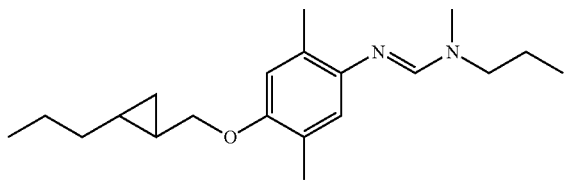 [SMILES: CCCC1CC1COc1cc(C)c(/N=C/N(C)CCC)cc1C]

¹H-NMR (CDCl₃) δ: 7.39 (1H, s), 6.60 (1H, s), 6.54 (1H, s), 3.76 (2H, ddd, J=62.9, 10.4, 7.1 Hz), 3.33-3.13 (2H, br m), 2.97 (3H, s), 2.21 (3H, s), 2.18 (3H, s), 1.65-1.58 (2H, m), 1.48-1.27 (3H, m), 1.22-1.11 (1H, m), 1.01-0.92 (1H, m), 0.93 (3H, t, J=7.3 Hz), 0.91 (3H, t, J=7.3 Hz), 0.75-0.66 (1H, m), 0.50-0.44 (1H, m), 0.39-0.33 (1H, m).

Production Example 14

A mixture of 0.11 g of 2,5-dimethyl-4-[(2,2,3,3-tetramethylcyclopropyl)methoxy]phenylamine, 0.01 g of p-toluenesulfonic acid monohydrate and 5 mL of trimethyl orthoformate was stirred under heating and refluxing for 2 hours. The cooled reaction mixture was concentrated under reduced pressure. The resulting residue and 5 mL of 1,4-dioxane were mixed at room temperature, and 0.5 mL of ethylmethylamine was added to the resulting mixture at room temperature. The resulting mixture was stirred at 80° C. for 2 hours. The reaction mixture was cooled to around room temperature, and then concentrated under reduced pressure. The resulting residue was subjected to silica gel column chromatography to obtain 0.07 g of N'-{2,5-dimethyl-4-[(2,2,3,3-tetramethylcyclopropyl)methoxy]phenyl}-N-ethyl-N-methylformamidine (Compound of Present Invention (1-14)).

Compound of Present Invention (1-14)

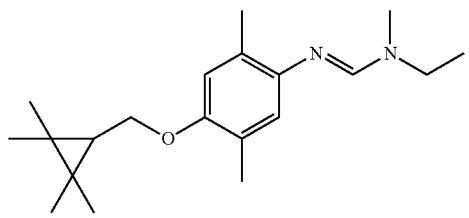 [SMILES: CCN(C)/C=N/c1cc(C)c(OCC2C(C)(C)C2(C)C)cc1C]

$^1$H-NMR (CDCl$_3$) δ: 7.39 (1H, s), 6.65 (1H, s), 6.54 (1H, s), 3.93 (2H, d, J=7.6 Hz), 3.41-3.27 (2H, br m), 2.97 (3H, s), 2.23 (3H, s), 2.18 (3H, s), 1.19 (3H, t, J=7.1 Hz), 1.12 (6H, s), 1.02 (6H, s), 0.70 (1H, t, J=7.3 Hz).

Production Example 15

A mixture of 0.09 g of 2,5-dimethyl-4-[(2,2,3,3-tetramethylcyclopropyl)methoxy]phenylamine, 0.01 g of p-toluenesulfonic acid monohydrate and 5 mL of trimethyl orthoformate was stirred under heating and refluxing for 2 hours. The cooled reaction mixture was concentrated under reduced pressure. The resulting residue and 5 mL of 1,4-dioxane were mixed at room temperature, and 0.5 mL of methylpropylamine was added to the resulting mixture at room temperature. The resulting mixture was stirred at 80° C. for 2 hours. The reaction mixture was cooled to around room temperature, and then concentrated under reduced pressure. The resulting residue was subjected to silica gel column chromatography to obtain 0.07 g of N'-{2,5-dimethyl-4-[(2,2,3,3-tetramethylcyclopropyl)methoxy]phenyl}-N-methyl-N-propylformamidine (Compound of Present Invention (1-15)).

Compound of Present Invention (1-15)

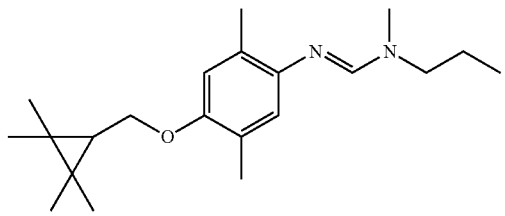 [SMILES: CCCN(C)/C=N/c1cc(C)c(OCC2C(C)(C)C2(C)C)cc1C]

$^1$H-NMR (CDCl$_3$) δ: 7.39 (1H, s), 6.65 (1H, s), 6.54 (1H, s), 3.93 (2H, d, J=7.6 Hz), 3.31-3.15 (2H, br m), 2.97 (3H, s), 2.22 (3H, s), 2.18 (3H, s), 1.65-1.59 (2H, m), 1.12 (6H, s), 1.02 (6H, s), 0.91 (3H, t, J=7.3 Hz), 0.70 (1H, t, J=7.4 Hz).

Production Example 16

A mixture of 0.19 g of 4-[(2,2-dibromocyclopropyl)methoxy)-2,5-dimethylphenylamine, 0.01 g of p-toluenesulfonic acid monohydrate and 5 mL of trimethyl orthoformate was stirred under heating and refluxing for 1 hour. The cooled reaction mixture was concentrated under reduced pressure. The resulting residue and 5 mL of 1,4-dioxane were mixed at room temperature, and 0.1 mL of ethylmethylamine was added to the resulting mixture at room temperature. The resulting mixture was stirred at 80° C. for 2 hours. The reaction mixture was cooled to around room temperature, and then concentrated under reduced pressure. The resulting residue was subjected to silica gel column chromatography to obtain 0.13 g of N'-{4-[(2,2-dibromocyclopropyl)methoxy]-2,5-dimethylphenyl}-N-ethyl-N-methylformamidine (Compound of Present Invention (1-16)).

Compound of Present Invention (1-16)

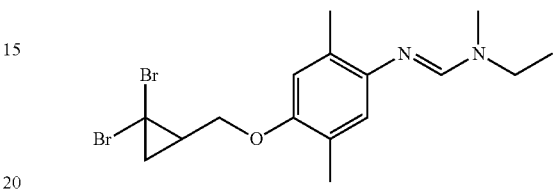

$^1$H-NMR (CDCl$_3$) δ: 7.39 (1H, s), 6.67 (1H, s), 6.56 (1H, s), 4.06 (2H, dd, J=6.6, 2.7 Hz), 3.44-3.24 (2H, br m), 2.97 (3H, s), 2.23 (3H, s), 2.22 (3H, s), 2.16-2.04 (1H, m), 1.88 (1H, dd, J=10.5, 7.6 Hz), 1.51 (1H, dd, J=7.6, 7.6 Hz), 1.19 (3H, t, J=7.2 Hz).

Production Example 17

A mixture of 0.23 g of 4-cyclopropylmethoxy-2,5-dimethylphenylamine and 10 mL of N,N-dimethylformamide dimethylacetal was stirred under heating and refluxing for 10 hours. The cooled reaction mixture was concentrated under reduced pressure. The resulting residue was subjected to silica gel column chromatography to obtain 0.18 g of N'-(4-cyclopropylmethoxy-2,5-dimethylphenyl)-N,N-dimethylformamidine (Compound of Present Invention (1-17)).

Compound of Present Invention (1-17)

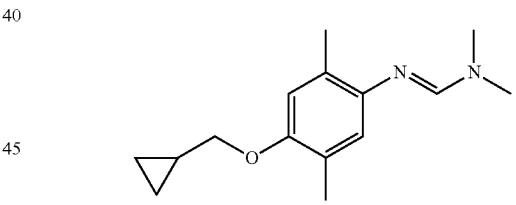

$^1$H-NMR (CDCl$_3$) δ: 7.38 (1H, s), 6.62 (1H, s), 6.54 (1H, s), 3.76 (2H, d, J=6.6 Hz), 2.98 (6H, s), 2.22 (3H, s), 2.19 (3H, s), 1.26-1.24 (1H, m), 0.61-0.56 (2H, m), 0.34-0.31 (2H, m).

Next, reference production examples for the production of a production intermediate of the compound of the present invention will be shown.

Reference Production Example 1

A mixture of 0.61 g of 2,5-dimethyl-1-[(1-methylcyclopropyl)methoxy]-4-nitrobenzene, 0.78 g of iron powder, 21 ml of acetic acid and 3 mL of water was stirred at 80° C. for 1 hour. The reaction mixture was cooled to around room temperature, and then concentrated under reduced pressure. The resulting residue was converted into basic with an aqueous 1 N sodium hydroxide solution, then ethyl acetate was added, and the mixture was filtered. The filtrate was extracted with ethyl acetate, and then the organic layer was washed with water and saturated salt water, and dried over anhydrous magnesium sulfate. The resulting residue was subjected to silica gel column chromatography to obtain 0.47 g of 2,5-dimethyl-4-[(1-methylcyclopropyl)methoxy]phenylamine.

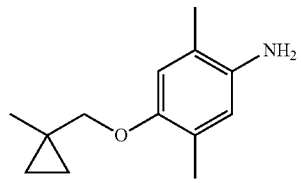

$^1$H-NMR (CDCl$_3$) δ: 6.53 (1H, s), 6.50 (1H, s), 3.64 (2H, s), 3.30 (2H, br s), 2.17 (3H, s), 2.12 (3H, s), 1.23 (3H, s), 0.52 (2H, dd, J=5.5, 4.5 Hz), 0.38 (2H, dd, J=5.6, 4.4 Hz).

Reference Production Example 2

A mixture of 1.73 g of 1-cyclopropylmethoxy-2,5-dimethyl-4-nitrobenzene, 2.18 g of iron powder, 30 mL of acetic acid and 30 mL of water was stirred at 80° C. for 1 hour. The reaction mixture was cooled to around room temperature, and then concentrated under reduced pressure. The resulting residue was converted into basic with an aqueous 1 N sodium hydroxide solution, then ethyl acetate was added, and the mixture was filtered. The filtrate was extracted with ethyl acetate, and then the organic layer was washed with water and saturated salt water, and dried over anhydrous magnesium sulfate. The resulting residue was subjected to silica gel column chromatography to obtain 0.84 g of 4-cyclopropylmethoxy-2,5-dimethylphenylamine.

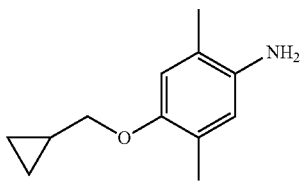

$^1$H-NMR (CDCl$_3$) δ: 6.58 (1H, s), 6.50 (1H, s), 3.72 (2H, d, J=6.6 Hz), 3.30 (2H, br s), 2.17 (3H, s), 2.12 (3H, s), 1.29-1.18 (1H, m), 0.62-0.55 (2H, m), 0.34-0.29 (2H, m).

Reference Production Example 3

A mixture of 0.70 g of 2,5-dimethyl-1-[(2-methylcyclopropyl)methoxy]-4-nitrobenzen e, 0.83 g of iron powder, 15 mL of acetic acid and 15 mL of water was stirred at 80° C. for 1 hour. The reaction mixture was cooled to around room temperature, and then concentrated under reduced pressure. The resulting residue was converted into basic with an aqueous 1 N sodium hydroxide solution, then ethyl acetate was added, and the mixture was filtered. The filtrate was extracted with ethyl acetate, and then the organic layer was washed with water and saturated salt water, and dried over anhydrous magnesium sulfate. The resulting residue was subjected to silica gel column chromatography to obtain 0.46 g of 2,5-dimethyl-4-[(2-methylcyclopropyl)methoxy]phenylamine.

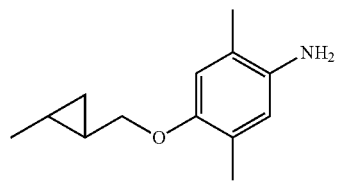

$^1$H-NMR (CDCl$_3$) δ: 6.57 (1H, s), 6.50 (1H, s), 3.77-3.67 (2H, m), 3.31 (2H, br s), 2.17 (3H, s), 2.13 (3H, s), 1.08 (3H, d, J=6.0 Hz), 0.98-0.88 (1H, m), 0.76-0.66 (1H, m), 0.50-0.43 (1H, m), 0.35-0.29 (1H, m).

Reference Production Example 4

A mixture of 0.97 g of 1-(1-cyclopropylethoxy)-2,5-dimethyl-4-nitrobenzene, 1.15 g of iron powder, 15 mL of acetic acid and 15 mL of water was stirred at 80° C. for 1 hour. The reaction mixture was cooled to around room temperature, and then concentrated under reduced pressure. The resulting residue was converted into basic with an aqueous 1 N sodium hydroxide solution, then ethyl acetate was added, and the mixture was filtered. The filtrate was extracted with ethyl acetate, and then the organic layer was washed with water and saturated salt water, and dried over anhydrous magnesium sulfate. The resulting residue was subjected to silica gel column chromatography to obtain 0.56 g of 4-(1-cyclopropylethoxy)-2,5-dimethylphenylamine.

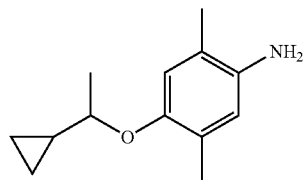

$^1$H-NMR (CDCl$_3$) δ: 6.60 (1H, s), 6.48 (1H, s), 3.58-3.50 (1H, m), 3.31 (2H, br s), 2.15 (3H, s), 2.11 (3H, s), 1.32 (3H, d, J=6.2 Hz), 1.12-1.01 (1H, m), 0.55-0.43 (2H, m), 0.36-0.28 (1H, m), 0.24-0.16 (1H, m).

Reference Production Example 5

A mixture of 1.58 g of 2,5-dimethyl-4-nitro-1-[(2-propylcyclopropyl)methoxy]benzene, 1.68 g of iron powder, 20 mL of acetic acid and 20 mL of water was stirred at 80° C. for 1 hour. The reaction mixture was cooled to around room temperature, and then concentrated under reduced pressure. The resulting residue was converted into basic with an aqueous 1 N sodium hydroxide solution, then ethyl acetate was added, and the mixture was filtered. The filtrate was extracted with ethyl acetate, and then the organic layer was washed with water and saturated salt water, and dried over anhydrous magnesium sulfate. The resulting residue was subjected to silica gel column chromatography to obtain 0.90 g of 2,5-dimethyl-4-[(2-propylcyclopropyl)methoxy]phenylamine.

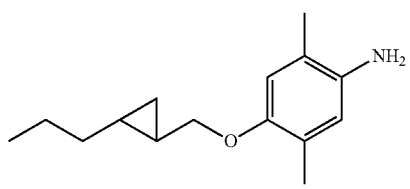 [SMILES: CCCC1CC1COc1cc(C)c(N)cc1C]

¹H-NMR (CDCl₃) δ: 6.55 (1H, s), 6.50 (1H, s), 3.78 (1H, dd, J=10.0, 6.5 Hz), 3.65 (1H, dd, J=10.1, 7.1 Hz), 3.29 (2H, br s), 2.16 (3H, s), 2.12 (3H, s), 1.48-1.37 (2H, m), 1.36-1.25 (1H, m), 1.24-1.12 (1H, m), 1.00-0.88 (1H, m), 0.93 (3H, t, J=7.3 Hz), 0.74-0.62 (1H, m), 0.49-0.42 (1H, m), 0.39-0.32 (1H, m).

Reference Production Example 6

A mixture of 0.34 g of 2,5-dimethyl-4-nitro-1-[(2,2,3,3-tetramethylcyclopropyl)methoxy]benzene, 0.34 g of iron powder, 5 mL of acetic acid and 5 mL of water was stirred at 80° C. for 1 hour. The reaction mixture was cooled to around room temperature, and then concentrated under reduced pressure. The resulting residue was converted into basic with an aqueous 1 N sodium hydroxide solution, then ethyl acetate was added, and the mixture was filtered. The filtrate was extracted with ethyl acetate, and then the organic layer was washed with water and saturated salt water, and dried over anhydrous magnesium sulfate. The resulting residue was subjected to silica gel column chromatography to obtain 0.24 g of 2,5-dimethyl-4-[(2,2,3,3-tetramethylcyclopropyl)methoxy]phenylamine.

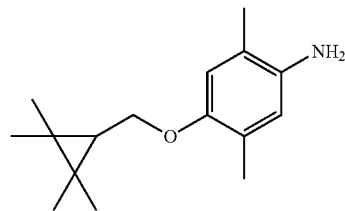 [SMILES: Cc1cc(OCC2C(C)(C)C2(C)C)c(C)cc1N]

¹H-NMR (CDCl₃) δ: 6.60 (1H, s), 6.50 (1H, s), 3.89 (2H, d, J=7.3 Hz), 3.30 (2H, br s), 2.16 (3H, s), 2.13 (3H, s), 1.12 (6H, s), 1.01 (6H, s), 0.69 (1H, d, J=7.3 Hz).

Reference Production Example 7

A mixture of 0.37 g of 1-[(2,2-dibromocyclopropyl)methoxy]-2,5-dimethyl-4-nitrobenzene, 0.29 g of iron powder, 20 mL of acetic acid and 5 mL of water was stirred at 80° C. for 1 hour. The reaction mixture was cooled to around room temperature, and then concentrated under reduced pressure. The resulting residue was converted into basic with an aqueous 1 N sodium hydroxide solution, then ethyl acetate was added, and the mixture was filtered. The filtrate was extracted with ethyl acetate, and then the organic layer was washed with water and saturated salt water, and dried over anhydrous magnesium sulfate. The resulting residue was subjected to silica gel column chromatography to obtain 0.19 g of 4-[(2,2-dibromocyclopropyl)methoxy]-2,5-dimethylphenylamine

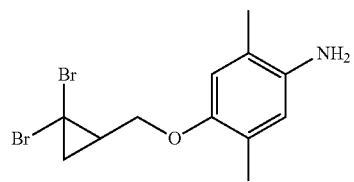

¹H-NMR (CDCl₃) δ: 6.62 (1H, s), 6.52 (1H, s), 4.06-3.97 (2H, m), 3.34 (2H, br s), 2.20 (3H, s), 2.14 (3H, s), 2.13-2.05 (1H, m), 1.90-1.84 (1H, m), 1.52-1.46 (1H, m).

Reference Production Example 8

2.98 g of Bis(2-methoxyethyl) azodicarboxylate was added to a mixture of 1.59 g of 2,5-dimethyl-4-nitrophenol, 0.81 g of (1-methylcyclopropyl)methanol, 2.98 g of triphenylphosphine and 50 mL of toluene at 0° C., and the mixture was stirred at 80° C. for 4 hours. After cooling, a saturated aqueous sodium bicarbonate solution was added, and the mixture was extracted with ethyl acetate, and then the organic layer was washed with water and saturated salt water and dried over anhydrous magnesium sulfate. The resulting residue was subjected to silica gel column chromatography to obtain 0.77 g of 2,5-dimethyl-1-[(1-methylcyclopropyl)methoxy]-4-nitrobenzene.

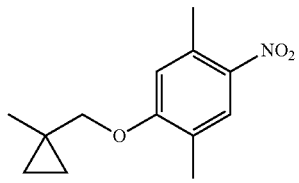

¹H-NMR (CDCl₃) δ: 7.93 (1H, s), 6.58 (1H, s), 3.80 (2H, s), 2.60 (3H, s), 2.25 (3H, s), 1.25 (3H, s), 0.57 (2H, dd, J=5.8, 4.6 Hz), 0.47 (2H, dd, J=5.8, 4.6 Hz).

Reference Production Example 9

3.15 g of Bis(2-methoxyethyl) azodicarboxylate was added to a mixture of 1.73 g of 2,5-dimethyl-4-nitrophenol, 0.75 g of cyclopropylmethanol, 3.26 g of triphenylphosphine and 100 mL of toluene at 0° C., and the mixture was stirred at 80° C. for 4 hours. After cooling, a saturated aqueous sodium bicarbonate solution was added, and the mixture was extracted with ethyl acetate, and then the organic layer was washed with water and saturated salt water and dried over anhydrous magnesium sulfate. The resulting residue was subjected to silica gel column chromatography to obtain 1.95 g of 1-cyclopropylmethoxy-2,5-dimethyl-4-nitrobenzene.

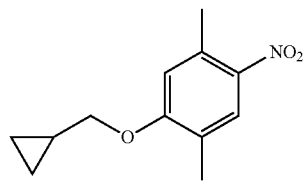

¹H-NMR (CDCl₃) δ: 7.93 (1H, s), 6.61 (1H, s), 3.89 (2H, d, J=6.8 Hz), 2.61 (3H, s), 2.24 (3H, s), 1.35-1.24 (1H, m), 0.70-0.63 (2H, m), 0.41-0.35 (2H, m).

Reference Production Example 10

2.55 g of Bis(2-methoxyethyl) azodicarboxylate was added to a mixture of 1.40 g of 2,5-dimethyl-4-nitrophenol, 0.72 g of (2-methylcyclopropyl)methanol, 2.64 g of triphenylphosphine and 100 mL of toluene at 0° C., and the mixture was stirred at 80° C. for 4 hours. After cooling, a saturated aqueous sodium bicarbonate solution was added, and the mixture was extracted with ethyl acetate, and then the organic layer was washed with water and saturated salt water and dried over anhydrous magnesium sulfate. The resulting residue was subjected to silica gel column chromatography to obtain 1.64 g of 2,5-dimethyl-1-[(2-methylcyclopropyl)methoxy]-4-nitrobenzen e.

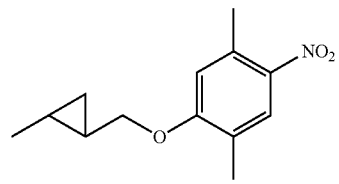 [SMILES: Cc1cc([N+](=O)[O-])c(C)cc1OCC1CC1C]

¹H-NMR (CDCl₃) δ: 7.93 (1H, s), 6.60 (1H, s), 3.89 (2H, d, J=6.8 Hz), 2.61 (3H, s), 2.24 (3H, s), 1.11 (3H, d, J=6.0 Hz), 1.03-0.94 (1H, m), 0.84-0.74 (1H, m), 0.57-0.51 (1H, m), 0.44-0.38 (1H, m).

Reference Production Example 11

3.10 g of Bis(2-methoxyethyl) azodicarboxylate was added to a mixture of 1.70 g of 2,5-dimethyl-4-nitrophenol, 0.88 g of (1-cyclopropyl) ethanol, 3.20 g of triphenylphosphine and 100 mL of toluene at 0° C., and the mixture was stirred at 80° C. for 4 hours. After cooling, a saturated aqueous sodium bicarbonate solution was added, and the mixture was extracted with ethyl acetate, and then the organic layer was washed with water and saturated salt water and dried over anhydrous magnesium sulfate. The resulting residue was subjected to silica gel column chromatography to obtain 1.09 g of 1-(1-cyclopropylethoxy)-2,5-dimethyl-4-nitrobenzene.

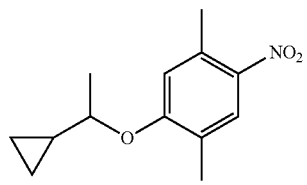 [SMILES: Cc1cc([N+](=O)[O-])c(C)cc1OC(C)C1CC1]

¹H-NMR (CDCl₃) δ: 7.93 (1H, s), 6.62 (1H, s), 4.06-3.97 (1H, m), 2.60 (3H, s), 2.21 (3H, s), 1.40 (3H, d, J=6.0 Hz), 1.21-1.10 (1H, m), 0.62-0.52 (2H, m), 0.43-0.27 (2H, m).

Reference Production Example 12

3.84 g of Bis(2-methoxyethyl) azodicarboxylate was added to a mixture of 2.11 g of 2,5-dimethyl-4-nitrophenol, 1.44 g of (2-propylcyclopropyl)methanol, 3.97 g of triphenylphosphine and 100 mL of toluene at 0° C., and the mixture was stirred at 80° C. for 4 hours. After cooling, a saturated aqueous sodium bicarbonate solution was added, and the mixture was extracted with ethyl acetate, and then the organic layer was washed with water and saturated salt water and dried over anhydrous magnesium sulfate. The resulting residue was subjected to silica gel column chromatography to obtain 2.52 g of 2,5-dimethyl-4-nitro-1-[(2-propylcyclopropyl)methoxy]benzene.

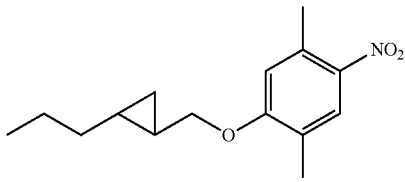 [SMILES: CCCC1CC1COc1cc(C)c([N+](=O)[O-])cc1C]

¹H-NMR (CDCl₃) δ: 7.93 (1H, s), 6.59 (1H, s), 4.01 (1H, dd, J=9.9, 6.4 Hz), 3.76 (1H, dd, J=9.9, 7.6 Hz), 2.61 (3H, s), 2.24 (3H, s), 1.49-1.35 (3H, m), 1.19-1.09 (1H, m), 1.06-0.97 (1H, m), 0.95 (3H, t, J=7.2 Hz), 0.81-0.72 (1H, m), 0.56-0.49 (1H, m), 0.48-0.41 (1H, m).

Reference Production Example 13

1.97 g of Bis(2-methoxyethyl) azodicarboxylate was added to a mixture of 1.08 g of 2,5-dimethyl-4-nitrophenol, 0.83 g of (2,2,3,3-tetramethylcyclopropyl)methanol, 2.04 g of triphenylphosphine and 100 mL of toluene at 0° C., and the mixture was stirred at 90° C. for 4 hours. After cooling, a saturated aqueous sodium bicarbonate solution was added, and the mixture was extracted with ethyl acetate, and then the organic layer was washed with water and saturated salt water and dried over anhydrous magnesium sulfate. The resulting residue was subjected to silica gel column chromatography to obtain 0.15 g of 2,5-dimethyl-4-nitro-1-[(2,2,3,3-tetramethylcyclopropyl) methoxy]benzene.

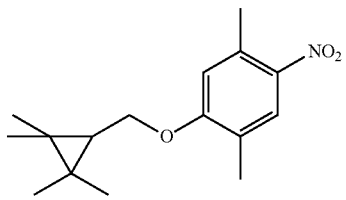 [SMILES: Cc1cc([N+](=O)[O-])c(C)cc1OCC1C(C)(C)C1(C)C]

¹H-NMR (CDCl₃) δ: 7.93 (1H, s), 6.64 (1H, s), 4.07 (2H, d, J=7.6 Hz), 2.62 (3H, s), 2.22 (3H, s), 1.15 (6H, s), 1.06 (6H, s), 0.74 (1H, t, J=7.6 Hz).

Reference Production Example 14

0.85 g of Bis(2-methoxyethyl) azodicarboxylate was added to a mixture of 0.47 g of 2,5-dimethyl-4-nitrophenol, 0.64 g of (2,2-dibromocyclopropyl)methanol (manufactured according to a reference document (R. Huwyler, A. Al-Dulayymi, M. Neuenschwander, Helv. Chim. Acta 1999, 82, 2336)), 0.87 g of triphenylphosphine and 30 mL of toluene at 0° C., and the mixture was stirred at 80° C. for 5 hours. After cooling, a saturated aqueous sodium bicarbonate solution was added, and the mixture was extracted with ethyl acetate, and then the organic layer was washed with water and saturated salt water and dried over anhydrous magnesium sulfate. The resulting residue was subjected to silica gel column chromatography to obtain 0.38 g of 1-[(2,2-dibromo-cyclopropyl)methoxy]-2,5-dimethyl-4-nitrobenzene.

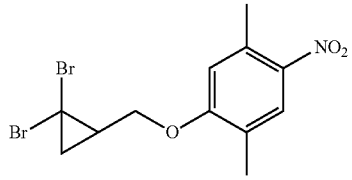 [SMILES: Cc1cc([N+](=O)[O-])c(C)cc1OCC1CC1(Br)Br]

¹H-NMR (CDCl₃) δ: 7.94 (1H, s), 6.65 (1H, s), 4.24 (1H, dd, J=10.5, 5.6 Hz), 4.12 (1H, dd, J=10.4, 7.9 Hz), 2.62 (3H, s), 2.28 (3H, s), 2.21-2.11 (1H, m), 1.99-1.93 (1H, m), 1.61-1.55 (1H, m).

According to the above methods, the followings can be obtained: Compounds AA-001 to AA-528, AB-001 to AB-528, AC-001 to AC-528, AD-001 to AD-528, AE-001 to AE-528, AF-001 to AF-528, AG-001 to AG-528, AH-001 to AH-528, AI-001 to AI-528, AJ-001 to AJ-528, AK-001 to AK-528, AL-001 to AL-528, AM-001 to AM-528, AN-001 to AN-528, AO-001 to AO-528, AP-001 to AP-528, AQ-001 to AQ-528, AR-001 to AR-528, AS-001 to AS-528, AT-001 to AT-528, AU-001 to AU-528, AV-001 to AV-528, AW-001 to AW-528, AX-001 to AX-528, AY-001 to AY-528, AZ-001 to AZ-528, AAA-001 to AAA-528, AAB-001 to AAB-528, AAC-001 to AAC-528, AAD-001 to AAD-528, AAE-001 to AAE-528, AAF-001 to AAF-528, AAG-001 to AAG-528, AAH-001 to AAH-528, AAI-001 to AAI-528, AAJ-001 to AAJ-528, AAK-001 to AAK-528, AAL-001 to AAL-528, AAM-001 to AAM-528, AAN-001 to AAN-528, AAO-001 to AAO-528, AAP-001 to AAP-528, AAQ-001 to AAQ-528, AAR-001 to AAR-528, AAS-001 to AAS-528, AAT-001 to AAT-528, AAU-001 to AAU-528, AAV-001 to AAV-528, AAW-001 to AAW-528, AAX-001 to AAX-528, AAY-001 to AAY-528, AAZ-001 to AAZ-528, ABA-001 to ABA-528, ABB-001 to ABB-528, ABC-001 to ABC-528, ABD-001 to ABD-528, ABE-001 to ABE-528, ABF-001 to ABF-528, ABG-001 to ABG-528, ABH-001 to ABH-528, ABI-001 to ABI-528, ABJ-001 to ABJ-528, ABK-001 to ABK-528, ABL-001 to ABL-528, ABM-001 to ABM-528, ABN-001 to ABN-528, ABO-001 to ABO-528, ABP-001 to ABP-528, ABQ-001 to ABQ-528, ABR-001 to ABR-528, ABS-001 to ABS-528, ABT-001 to ABT-528, ABU-001 to ABU-528, ABV-001 to ABV-528, ABW-001 to ABW-528, ABX-001 to ABX-528, ABY-001 to ABY-528, ABZ-001 to ABZ-528, ACA-001 to ACA-528, ACB-001 to ACB-528, ACC-001 to ACC-528, ACD-001 to ACD-528, ACE-001 to ACE-528, ACF-001 to ACF-528, ACG-001 to ACG-528, ACH-001 to ACH-528, ACI-001 to ACI-528, ACJ-001 to ACJ-528, ACK-001 to ACK-528, ACL-001 to ACL-528, ACM-001 to ACM-528, ACN-001 to ACN-528, ACO-001 to ACO-528, ACP-001 to ACP-528, ACQ-001 to ACQ-528, ACR-001 to ACR-528, ACS-001 to ACS-528, ACT-001 to ACT-528, ACU-001 to ACU-528, ACV-001 to ACV-528, ACW-001 to ACW-528, ACX-001 to ACX-528, ACY-001 to ACY-528, ACZ-001 to ACZ-528, ADA-001 to ADA-528, ADB-001 to ADB-528, ADC-001 to ADC-528, ADD-001 to ADD-528, ADE-001 to ADE-528, ADF-001 to ADF-528, ADG-001 to ADG-528, and ADH-001 to ADH-528.

Compounds AA-001 to AA-528 are each an amidine compound represented by

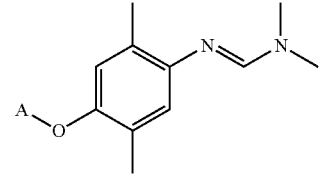

wherein A is a substituent corresponding to each of Substitution Numbers 1 to 528 listed in Table 1 to Table 18, Compounds AB-001 to AB-528 are each an amidine compound represented by

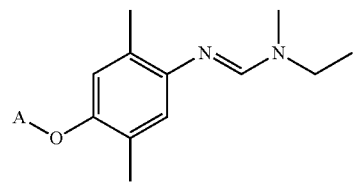

wherein A is a substituent corresponding to each of Substitution Numbers 1 to 528 listed in Table 1 to Table 18, Compounds AC-001 to AC-528 are each an amidine compound represented by

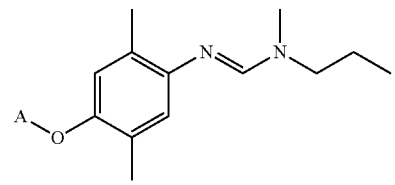

wherein A is a substituent corresponding to each of Substitution Numbers 1 to 528 listed in Table 1 to Table 18, Compounds AD-001 to AD-528 are each an amidine compound represented by

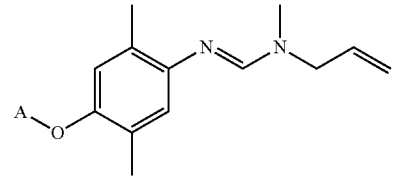

wherein A is a substituent corresponding to each of Substitution Numbers 1 to 528 listed in Table 1 to Table 18.

Compounds AE-001 to AE-528 are each an each amidine compound represented by

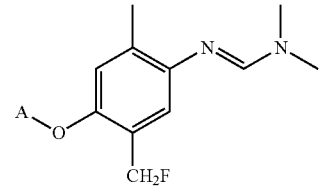

wherein A is a substituent corresponding to each of Substitution Numbers 1 to 528 listed in Table 1 to Table 18, Compounds AF-001 to AF-528 are each an amidine compound represented by

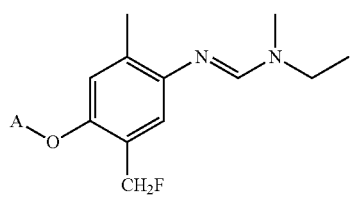

wherein A is a substituent corresponding to each of Substitution Numbers 1 to 528 listed in Table 1 to Table 18, Compounds AG-001 to AG-528 are each an amidine compound represented by

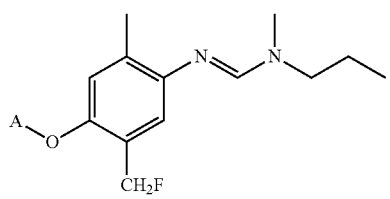

wherein A is a substituent corresponding to each of Substitution Numbers 1 to 528 listed in Table 1 to Table 18, Compounds AH-001 to AH-528 are each an amidine compound represented by

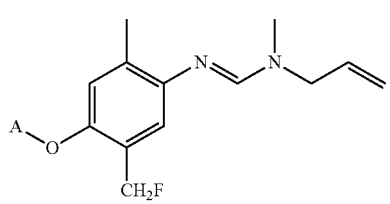

wherein A is a substituent corresponding to each of Substitution Numbers 1 to 528 listed in Table 1 to Table 18.

Compounds AI-001 to AI-528 are each an amidine compound

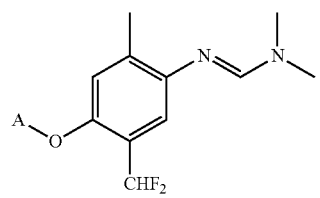

wherein A is a substituent corresponding to each of Substitution Numbers 1 to 528 listed in Table 1 to Table 18, Compounds AJ-001 to AJ-528 are each an amidine compound represented by

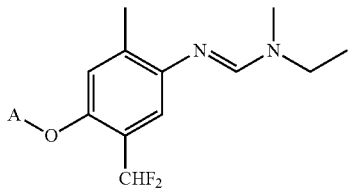

wherein A is a substituent corresponding to each of Substitution Numbers 1 to 528 listed in Table 1 to Table 18, Compounds AK-001 to AK-528 are each an amidine compound represented by

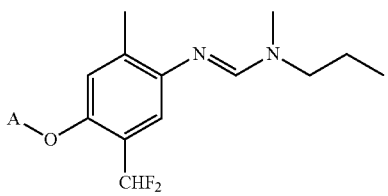

wherein A is a substituent corresponding to each of Substitution Numbers 1 to 528 listed in Table 1 to Table 18, Compounds AL-001 to AL-528 are each an amidine compound represented by

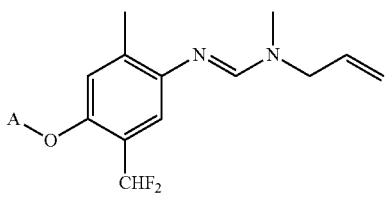

wherein A is a substituent corresponding to each of Substitution Numbers 1 to 528 listed in Table 1 to Table 18.

Compounds AM-001 to AM-528 are each an amidine compound represented by

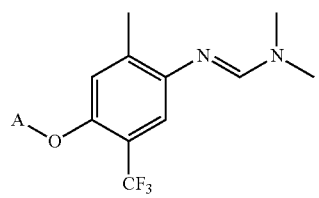

wherein A is a substituent corresponding to each of Substitution Numbers 1 to 528 listed in Table 1 to Table 18, Compounds AN-001 to AN-528 are each an amidine compound represented by

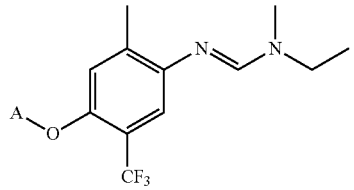

wherein A is a substituent corresponding to each of Substitution Numbers 1 to 528 listed in Table 1 to Table 18, Compounds AO-001 to AO-528 are each an amidine compound represented by

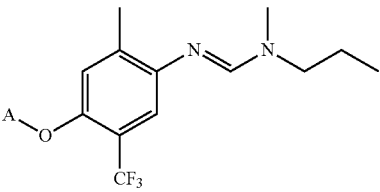

wherein A is a substituent corresponding to each of Substitution Numbers 1 to 528 listed in Table 1 to Table 18, Compounds AP-001 to AP-528 are each an amidine compound

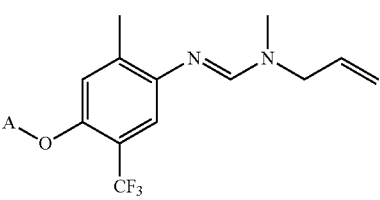

wherein A is a substituent corresponding to each of Substitution Numbers 1 to 528 listed in Table 1 to Table 18.

Compounds AQ-001 to AQ-528 are each an amidine compound represented by

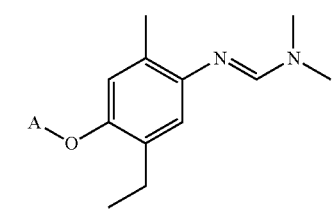

wherein A is a substituent corresponding to each of Substitution Numbers 1 to 528 listed in Table 1 to Table 18, Compounds AR-001 to AR-528 are each an amidine compound represented by

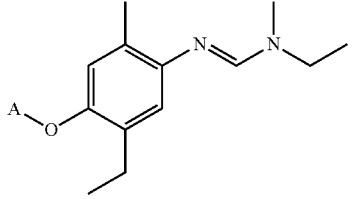

wherein A is a substituent corresponding to each of Substitution Numbers 1 to 528 listed in Table 1 to Table 18, Compounds AS-001 to AS-528 are each an amidine compound represented by

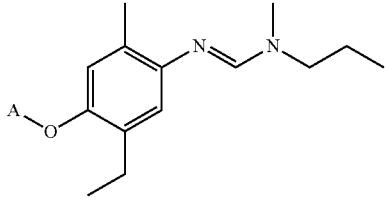

wherein A is a substituent corresponding to each of Substitution Numbers 1 to 528 listed in Table 1 to Table 18, Compounds AT-001 to AT-528 are each an amidine compound represented by

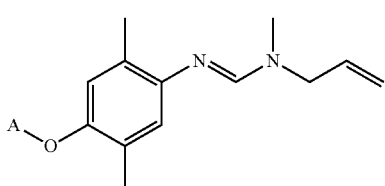

wherein A is a substituent corresponding to each of Substitution Numbers 1 to 528 listed in Table 1 to Table 18.

Compounds AU-001 to AU-528 are each an amidine compound represented by

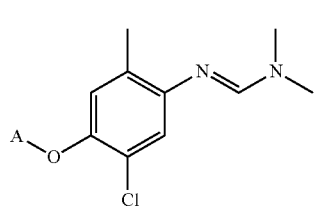

wherein A is a substituent corresponding to each of Substitution Numbers 1 to 528 listed in Table 1 to Table 18, Compounds AV-001 to AV-528 are each an amidine compound represented by

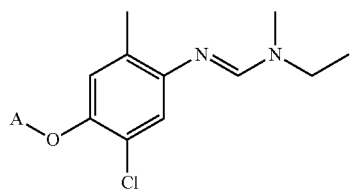

wherein A is a substituent corresponding to each of Substitution Numbers 1 to 528 listed in Table 1 to Table 18, Compounds AW-001 to AW-528 are each an amidine compound represented by

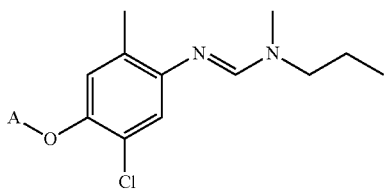

wherein A is a substituent corresponding to each of Substitution Numbers 1 to 528 listed in Table 1 to Table 18, Compounds AX-001 to AX-528 are each an amidine compound represented by

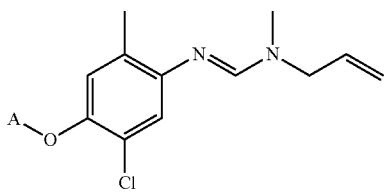

wherein A is a substituent corresponding to each of Substitution Numbers 1 to 528 listed in Table 1 to Table 18.

Compounds AY-001 to AY-528 are each an amidine compound represented by

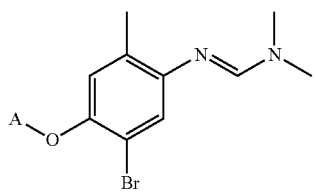

wherein A is a substituent corresponding to each of Substitution Numbers 1 to 528 listed in Table 1 to Table 18, Compounds AZ-001 to AZ-528 are each an amidine compound

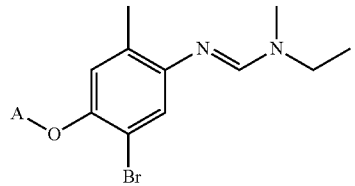

wherein A is a substituent corresponding to each of Substitution Numbers 1 to 528 listed in Table 1 to Table 18, Compounds AAA-001 to AAA-528 are each an amidine compound represented by

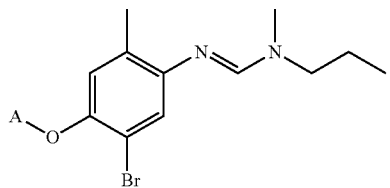

wherein A is a substituent corresponding to each of Substitution Numbers 1 to 528 listed in Table 1 to Table 18, Compounds AAB-001 to AAB-528 are each an amidine compound represented by

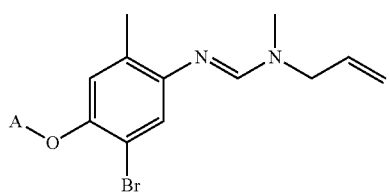

wherein A is a substituent corresponding to each of Substitution Numbers 1 to 528 listed in Table 1 to Table 18.

Compounds AAC-001 to AAC-528 are each an amidine compound represented by

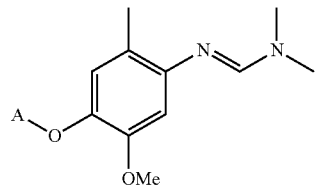

wherein A is a substituent corresponding to each of Substitution Numbers 1 to 528 listed in Table 1 to Table 18, Compounds AAD-001 to AAD-528 are each an amidine compound represented by

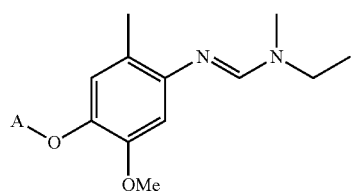

wherein A is a substituent corresponding to each of Substitution Numbers 1 to 528 listed in Table 1 to Table 18, Compounds AAE-001 to AAE-528 are each an amidine compound represented by

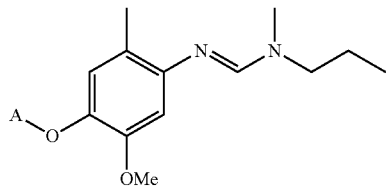

wherein A is a substituent corresponding to each of Substitution Numbers 1 to 528 listed in Table 1 to Table 18, Compounds AAF-001 to AAF-528 are each an amidine compound represented by

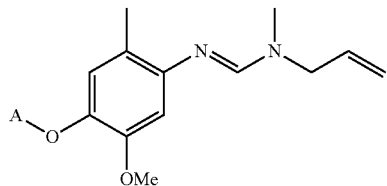

wherein A is a substituent corresponding to each of Substitution Numbers 1 to 528 listed in Table 1 to Table 18.

Compounds AAG-001 to AAG-528 are each an amidine compound represented by

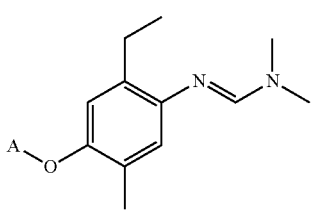

wherein A is a substituent corresponding to each of Substitution Numbers 1 to 528 listed in Table 1 to Table 18, Compounds AAH-001 to AAH-528 are each an amidine compound represented by

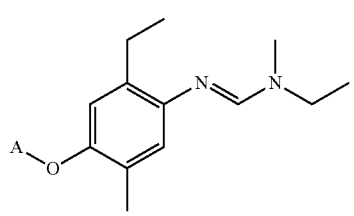

wherein A is a substituent corresponding to each of Substitution Numbers 1 to 528 listed in Table 1 to Table 18, Compounds AAI-001 to AAI-528 are each an amidine compound represented by

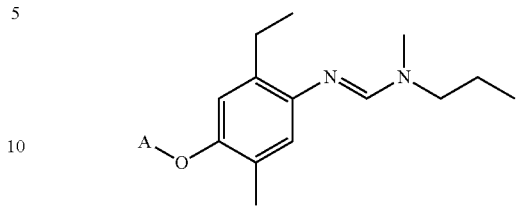

wherein A is a substituent corresponding to each of Substitution Numbers 1 to 528 listed in Table 1 to Table 18, Compounds AAJ-001 to AAJ-528 are each an amidine compound represented by

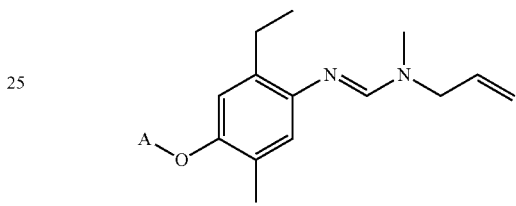

wherein A is a substituent corresponding to each of Substitution Numbers 1 to 528 listed in Table 1 to Table 18.

Compounds AAK-001 to AAK-528 are each an amidine compound represented by

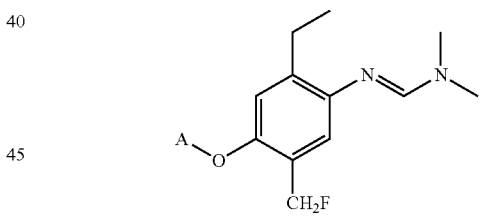

wherein A is a substituent corresponding to each of Substitution Numbers 1 to 528 listed in Table 1 to Table 18, Compounds AAL-001 to AAL-528 are each an amidine compound represented by

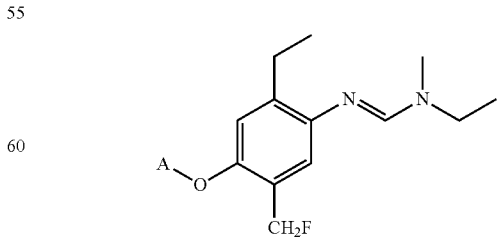

wherein A is a substituent corresponding to each of Substitution Numbers 1 to 528 listed in Table 1 to Table 18, Compounds AAM-001 to AAM-528 are each an amidine compound represented by

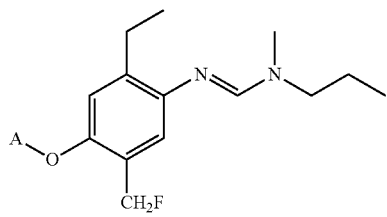

wherein A is a substituent corresponding to each of Substitution Numbers 1 to 528 listed in Table 1 to Table 18, Compounds AAN-001 to AAN-528 are each an amidine compound represented by

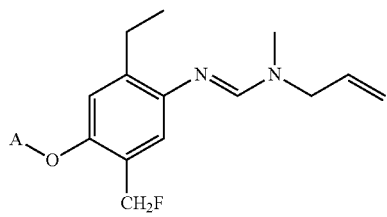

wherein A is a substituent corresponding to each of Substitution Numbers 1 to 528 listed in Table 1 to Table 18.

Compounds AAO-001 to AAO-528 are each an amidine compound represented by

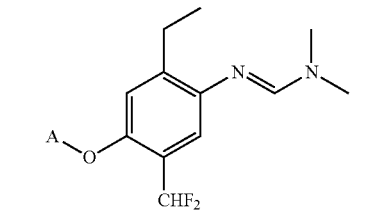

wherein A is a substituent corresponding to each of Substitution Numbers 1 to 528 listed in Table 1 to Table 18, Compounds AAP-001 to AAP-528 are each an amidine compound represented by

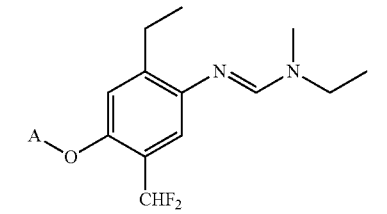

wherein A is a substituent corresponding to each of Substitution Numbers 1 to 528 listed in Table 1 to Table 18, Compounds AAQ-001 to AAQ-528 are each an amidine compound

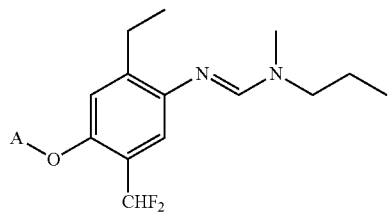

wherein A is a substituent corresponding to each of Substitution Numbers 1 to 528 listed in Table 1 to Table 18, Compounds AAR-001 to AAR-528 are each an amidine compound represented by

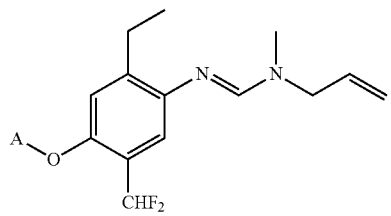

wherein A is a substituent corresponding to each of Substitution Numbers 1 to 528 listed in Table 1 to Table 18.

Compounds AAS-001 to AAS-528 are each an amidine compound represented by

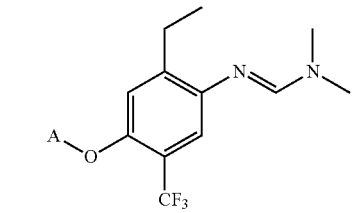

wherein A is a substituent corresponding to each of Substitution Numbers 1 to 528 listed in Table 1 to Table 18, Compounds AAT-001 to AAT-528 are each an amidine compound represented by

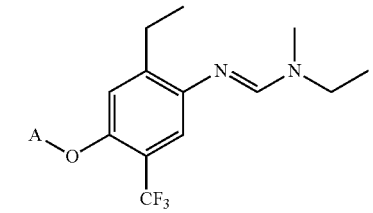

wherein A is a substituent corresponding to each of Substitution Numbers 1 to 528 listed in Table 1 to Table 18, Compounds AAU-001 to AAU-528 are each an amidine compound represented by

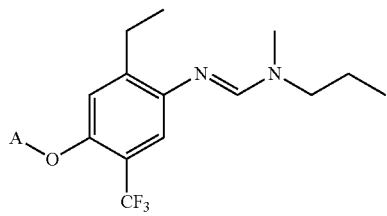

wherein A is a substituent corresponding to each of Substitution Numbers 1 to 528 listed in Table 1 to Table 18, Compounds AAV-001 to AAV-528 are each an amidine compound represented by

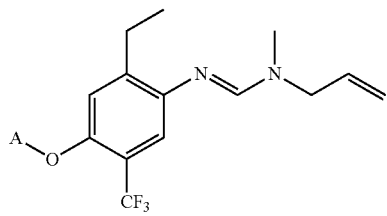

wherein A is a substituent corresponding to each of Substitution Numbers 1 to 528 listed in Table 1 to Table 18.

Compounds AAW-001 to AAW-528 are each an amidine compound represented by

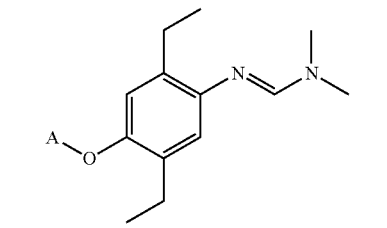

wherein A is a substituent corresponding to each of Substitution Numbers 1 to 528 listed in Table 1 to Table 18, Compounds AAX-001 to AAX-528 are each an amidine compound represented by

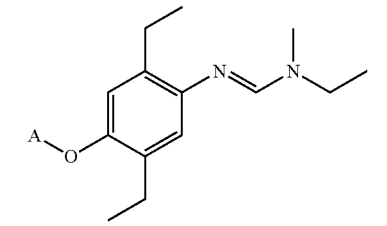

wherein A is a substituent corresponding to each of Substitution Numbers 1 to 528 listed in Table 1 to Table 18, Compounds AAY-001 to AAY-528 are each an amidine compound represented by

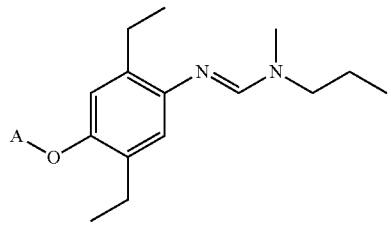

wherein A is a substituent corresponding to each of Substitution Numbers 1 to 528 listed in Table 1 to Table 18, Compounds AAZ-001 to AAZ-528 are each an amidine compound represented by

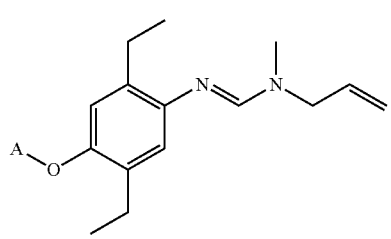

wherein A is a substituent corresponding to each of Substitution Numbers 1 to 528 listed in Table 1 to Table 18.

Compounds ABA-001 to ABA-528 are each an amidine compound

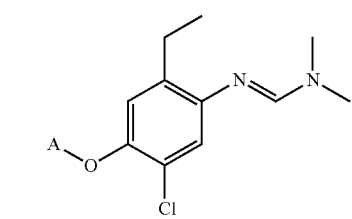

wherein A is a substituent corresponding to each of Substitution Numbers 1 to 528 listed in Table 1 to Table 18, Compounds ABB-001 to ABB-528 are each an amidine compound represented by

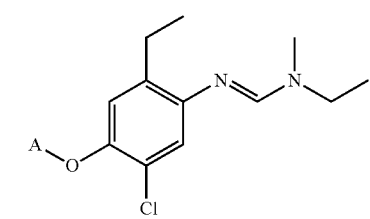

wherein A is a substituent corresponding to each of Substitution Numbers 1 to 528 listed in Table 1 to Table 18, Compounds ABC-001 to ABC-528 are each an amidine compound represented by

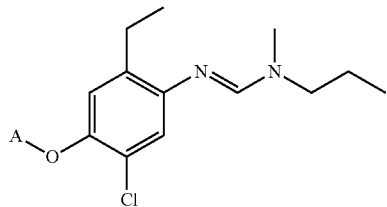

wherein A is a substituent corresponding to each of Substitution Numbers 1 to 528 listed in Table 1 to Table 18, Compounds ABD-001 to ABD-528 are each an amidine compound represented by

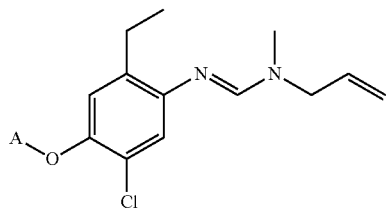

wherein A is a substituent corresponding to each of Substitution Numbers 1 to 528 listed in Table 1 to Table 18.

Compounds ABE-001 to ABE-528 are each an amidine compound represented by

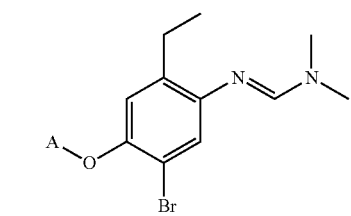

wherein A is a substituent corresponding to each of Substitution Numbers 1 to 528 listed in Table 1 to Table 18, Compounds ABF-001 to ABF-528 are each an amidine compound represented by

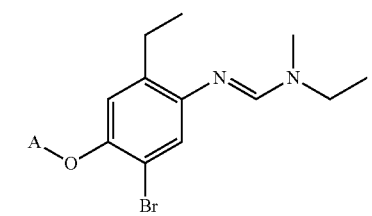

wherein A is a substituent corresponding to each of Substitution Numbers 1 to 528 listed in Table 1 to Table 18, Compounds ABG-001 to ABG-528 are each an amidine compound represented by

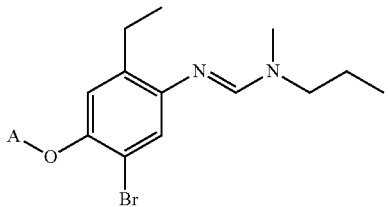

wherein A is a substituent corresponding to each of Substitution Numbers 1 to 528 listed in Table 1 to Table 18, Compounds ABH-001 to ABH-528 are each an amidine compound

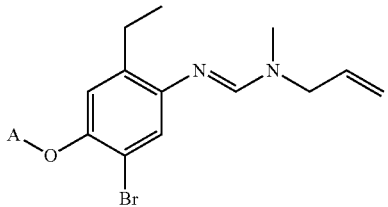

wherein A is a substituent corresponding to each of Substitution Numbers 1 to 528 listed in Table 1 to Table 18.

Compounds ABI-001 to ABI-528 are each an amidine compound represented by

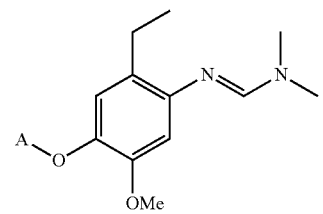

wherein A is a substituent corresponding to each of Substitution Numbers 1 to 528 listed in Table 1 to Table 18, Compounds ABJ-001 to ABJ-528 are each an amidine compound represented by

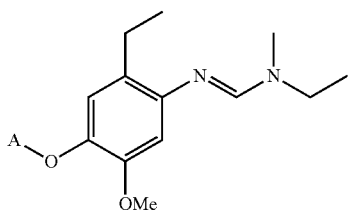

wherein A is a substituent corresponding to each of Substitution Numbers 1 to 528 listed in Table 1 to Table 18, Compounds ABK-001 to ABK-528 are each an amidine compound

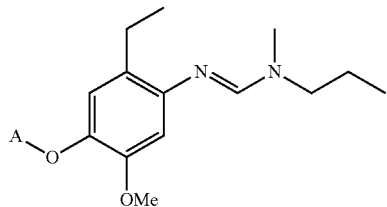

wherein A is a substituent corresponding to each of Substitution Numbers 1 to 528 listed in Table 1 to Table 18, Compounds ABL-001 to ABL-528 are each an amidine compound represented by

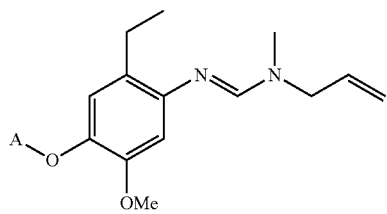

wherein A is a substituent corresponding to each of Substitution Numbers 1 to 528 listed in Table 1 to Table 18.

Compounds ABM-001 to ABM-528 are each an amidine compound represented by

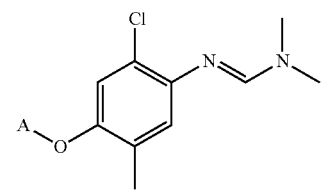

wherein A is a substituent corresponding to each of Substitution Numbers 1 to 528 listed in Table 1 to Table 18, Compounds ABN-001 to ABN-528 are each an amidine compound represented by

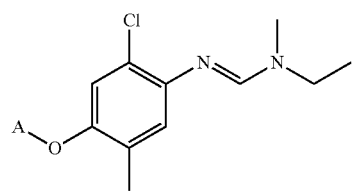

wherein A is a substituent corresponding to each of Substitution Numbers 1 to 528 listed in Table 1 to Table 18, Compounds ABO-001 to ABO-528 are each an amidine compound represented by

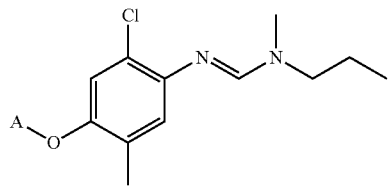

wherein A is a substituent corresponding to each of Substitution Numbers 1 to 528 listed in Table 1 to Table 18, Compounds ABP-001 to ABP-528 are each an amidine compound represented by

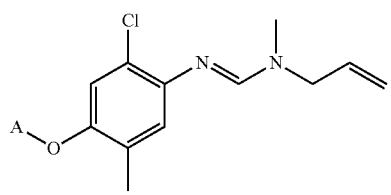

wherein A is a substituent corresponding to each of Substitution Numbers 1 to 528 listed in Table 1 to Table 18.

Compounds ABQ-001 to ABQ-528 are each an amidine compound represented by

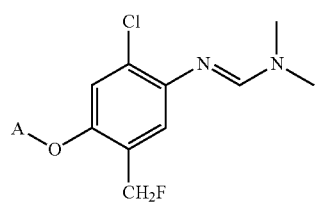

wherein A is a substituent corresponding to each of Substitution Numbers 1 to 528 listed in Table 1 to Table 18, Compounds ABR-001 to ABR-528 are each an amidine compound represented by

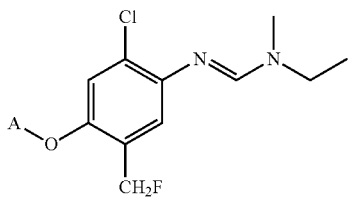

wherein A is a substituent corresponding to each of Substitution Numbers 1 to 528 listed in Table 1 to Table 18, Compounds ABS-001 to ABS-528 are each an amidine compound represented by

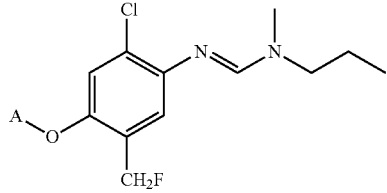

wherein A is a substituent corresponding to each of Substitution Numbers 1 to 528 listed in Table 1 to Table 18, Compounds ABT-001 to ABT-528 are each an amidine compound represented by

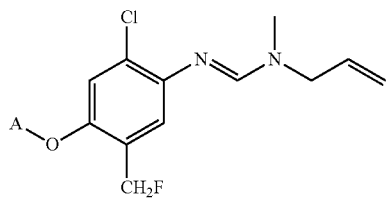

wherein A is a substituent corresponding to each of Substitution Numbers 1 to 528 listed in Table 1 to Table 18.

Compounds ABU-001 to ABU-528 are each an amidine compound

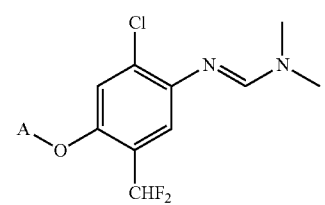

wherein A is a substituent corresponding to each of Substitution Numbers 1 to 528 listed in Table 1 to Table 18, Compounds ABV-001 to ABV-528 are each an amidine compound represented by

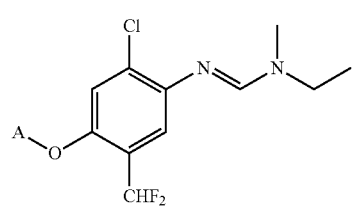

wherein A is a substituent corresponding to each of Substitution Numbers 1 to 528 listed in Table 1 to Table 18, Compounds ABW-001 to ABW-528 are each an amidine compound represented by

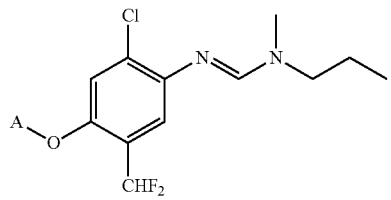

wherein A is a substituent corresponding to each of Substitution Numbers 1 to 528 listed in Table 1 to Table 18, Compounds ABX-001 to ABX-528 are each an amidine compound represented by

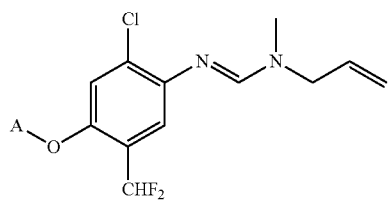

wherein A is a substituent corresponding to each of Substitution Numbers 1 to 528 listed in Table 1 to Table 18.

Compounds ABY-001 to ABY-528 are each an amidine compound represented by

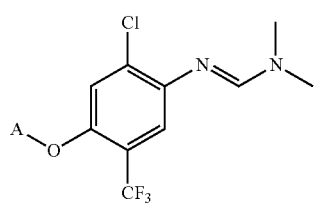

wherein A is a substituent corresponding to each of Substitution Numbers 1 to 528 listed in Table 1 to Table 18, Compounds ABZ-001 to ABZ-528 are each an amidine compound represented by

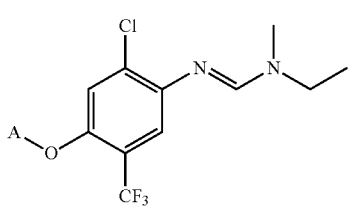

wherein A is a substituent corresponding to each of Substitution Numbers 1 to 528 listed in Table 1 to Table 18, Compounds ACA-001 to ACA-528 are each an amidine compound represented by

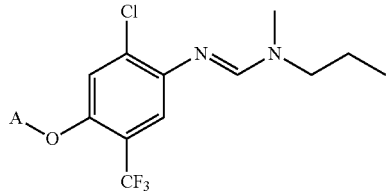

wherein A is a substituent corresponding to each of Substitution Numbers 1 to 528 listed in Table 1 to Table 18, Compounds ACB-001 to ACB-528 are each an amidine compound

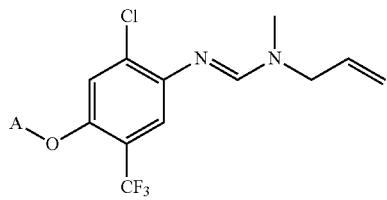

wherein A is a substituent corresponding to each of Substitution Numbers 1 to 528 listed in Table 1 to Table 18.

Compounds ACC-001 to ACC-528 are each an amidine compound represented by

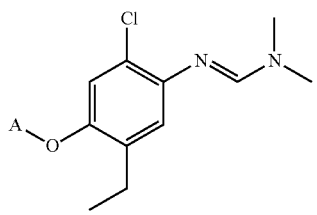

wherein A is a substituent corresponding to each of Substitution Numbers 1 to 528 listed in Table 1 to Table 18, Compounds ACD-001 to ACD-528 are each an amidine compound represented by

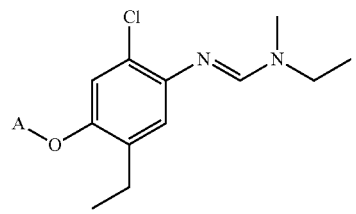

wherein A is a substituent corresponding to each of Substitution Numbers 1 to 528 listed in Table 1 to Table 18, Compounds ACE-001 to ACE-528 are each an amidine compound

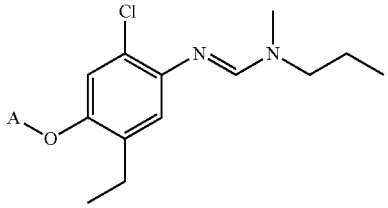

wherein A is a substituent corresponding to each of Substitution Numbers 1 to 528 listed in Table 1 to Table 18, Compounds ACF-001 to ACF-528 are each an amidine compound represented by

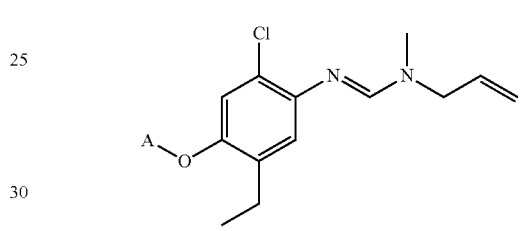

wherein A is a substituent corresponding to each of Substitution Numbers 1 to 528 listed in Table 1 to Table 18.

Compounds ACG-001 to ACG-528 are each an amidine compound represented by

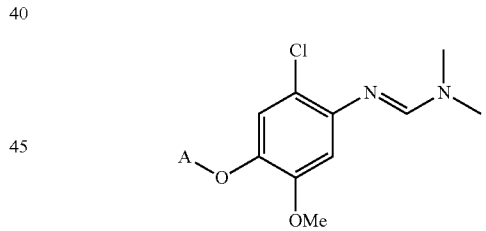

wherein A is a substituent corresponding to each of Substitution Numbers 1 to 528 listed in Table 1 to Table 18, Compounds ACH-001 to ACH-528 are each an amidine compound represented by wherein A is a substituent corresponding to each of Substitution Numbers 1 to 528 listed in Table 1 to Table 18, Compounds ACI-001 to ACI-528 are each an amidine compound represented by

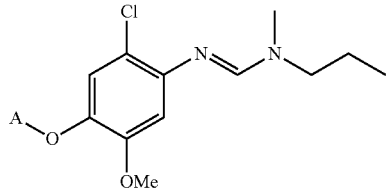

wherein A is a substituent corresponding to each of Substitution Numbers 1 to 528 listed in Table 1 to Table 18, Compounds ACJ-001 to ACJ-528 are each an amidine compound represented by

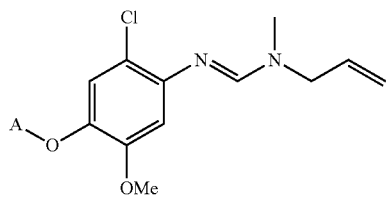

wherein A is a substituent corresponding to each of Substitution Numbers 1 to 528 listed in Table 1 to Table 18.

Compounds ACK-001 to ACK-528 are each an amidine compound represented by

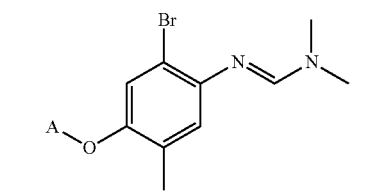

wherein A is a substituent corresponding to each of Substitution Numbers 1 to 528 listed in Table 1 to Table 18, Compounds ACL-001 to ACL-528 are each an amidine compound represented by

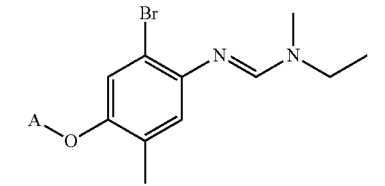

wherein A is a substituent corresponding to each of Substitution Numbers 1 to 528 listed in Table 1 to Table 18, Compounds ACM-001 to ACM-528 are each an amidine compound represented by

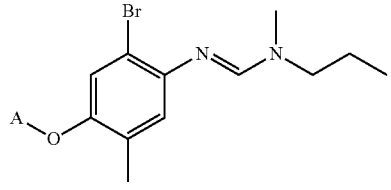

wherein A is a substituent corresponding to each of Substitution Numbers 1 to 528 listed in Table 1 to Table 18, Compounds ACN-001 to ACN-528 are each an amidine compound represented by

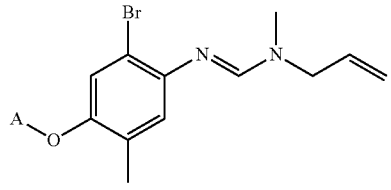

wherein A is a substituent corresponding to each of Substitution Numbers 1 to 528 listed in Table 1 to Table 18.

Compounds ACO-001 to ACO-528 are each an amidine compound

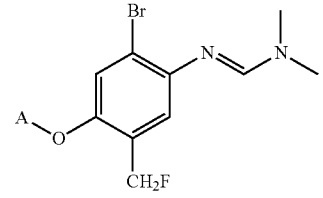

wherein A is a substituent corresponding to each of Substitution Numbers 1 to 528 listed in Table 1 to Table 18, Compounds ACP-001 to ACP-528 are each an amidine compound represented by

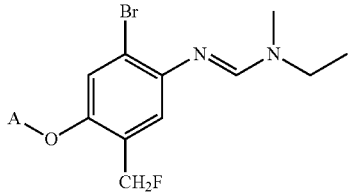

wherein A is a substituent corresponding to each of Substitution Numbers 1 to 528 listed in Table 1 to Table 18, Compounds ACQ-001 to ACQ-528 are each an amidine compound represented by

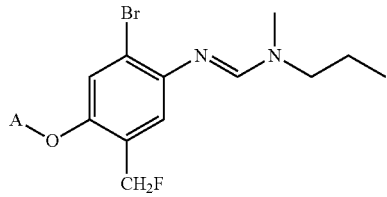

wherein A is a substituent corresponding to each of Substitution Numbers 1 to 528 listed in Table 1 to Table 18, Compounds ACR-001 to ACR-528 are each an amidine compound represented by

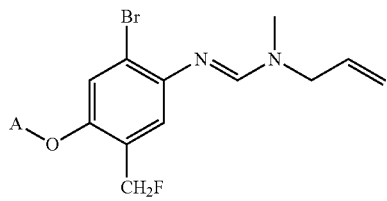

wherein A is a substituent corresponding to each of Substitution Numbers 1 to 528 listed in Table 1 to Table 18.

Compounds ACS-001 to ACS-528 are each an amidine compound represented by

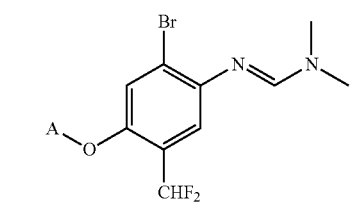

wherein A is a substituent corresponding to each of Substitution Numbers 1 to 528 listed in Table 1 to Table 18, Compounds ACT-001 to ACT-528 are each an amidine compound represented by

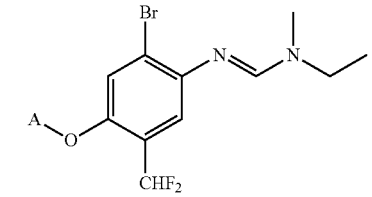

wherein A is a substituent corresponding to each of Substitution Numbers 1 to 528 listed in Table 1 to Table 18, Compounds ACU-001 to ACU-528 are each an amidine compound represented by

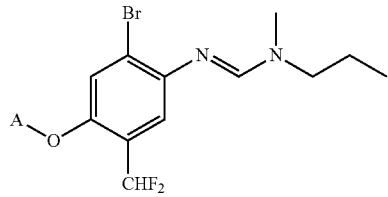

wherein A is a substituent corresponding to each of Substitution Numbers 1 to 528 listed in Table 1 to Table 18, Compounds ACV-001 to ACV-528 are each an amidine compound

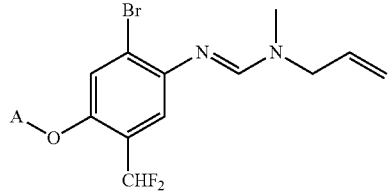

wherein A is a substituent corresponding to each of Substitution Numbers 1 to 528 listed in Table 1 to Table 18.

Compounds ACW-001 to ACW-528 are each an amidine compound represented by

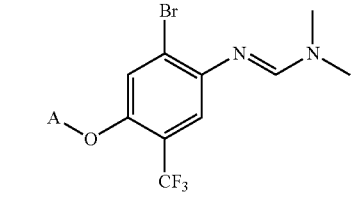

wherein A is a substituent corresponding to each of Substitution Numbers 1 to 528 listed in Table 1 to Table 18, Compounds ACX-001 to ACX-528 are each an amidine compound represented by

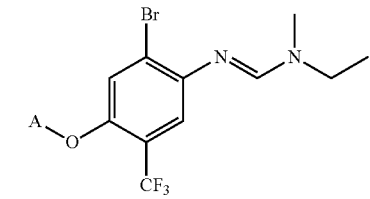

wherein A is a substituent corresponding to each of Substitution Numbers 1 to 528 listed in Table 1 to Table 18, Compounds ACY-001 to ACY-528 are each an amidine compound represented by

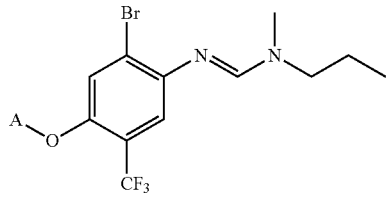

wherein A is a substituent corresponding to each of Substitution Numbers 1 to 528 listed in Table 1 to Table 18, Compounds ACZ-001 to ACZ-528 are each an amidine compound represented by

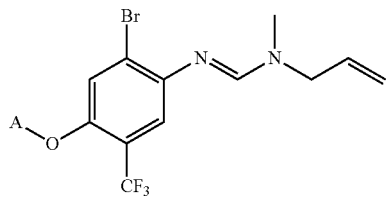

wherein A is a substituent corresponding to each of Substitution Numbers 1 to 528 listed in Table 1 to Table 18.

Compounds ADA-001 to ADA-528 are each an amidine compound represented by

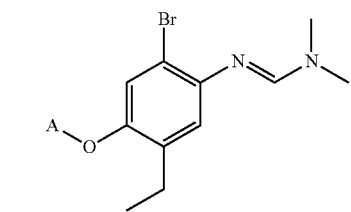

wherein A is a substituent corresponding to each of Substitution Numbers 1 to 528 listed in Table 1 to Table 18, Compounds ADB-001 to ADB-528 are each an amidine compound represented by

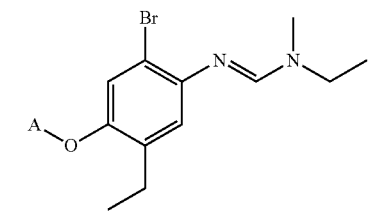

wherein A is a substituent corresponding to each of Substitution Numbers 1 to 528 listed in Table 1 to Table 18, Compounds ADC-001 to ADC-528 are each an amidine compound represented by

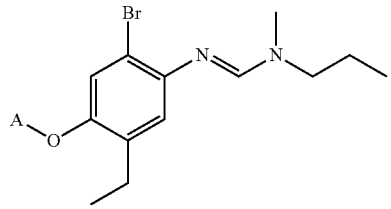

wherein A is a substituent corresponding to each of Substitution Numbers 1 to 528 listed in Table 1 to Table 18, Compounds ADD-001 to ADD-528 are each an amidine compound represented by

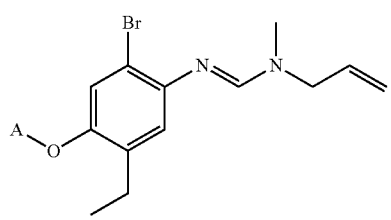

wherein A is a substituent corresponding to each of Substitution Numbers 1 to 528 listed in Table 1 to Table 18.

Compounds ADE-001 to ADE-528 are each an amidine compound represented by

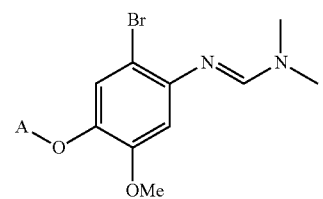

wherein A is a substituent corresponding to each of Substitution Numbers 1 to 528 listed in Table 1 to Table 18, Compounds ADF-001 to ADF-528 are each an amidine compound

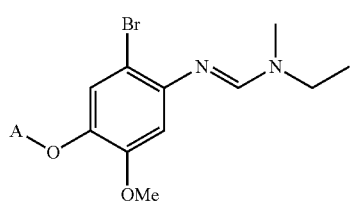

wherein A is a substituent corresponding to each of Substitution Numbers 1 to 528 listed in Table 1 to Table 18, Compounds ADG-001 to ADG-528 are each an amidine compound represented by

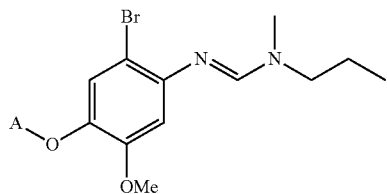

wherein A is a substituent corresponding to each of Substitution Numbers 1 to 528 listed in Table 1 to Table 18, Compounds ADH-001 to ADH-528 are each an amidine compound represented by

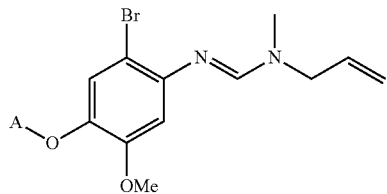

wherein A is a substituent corresponding to each of Substitution Numbers 1 to 528 listed in Table 1 to Table 18.
● in Table 1 to Table 18 represents a binding site.

TABLE 1

| Substituent Number | A |
|---|---|
| 1 |  |
| 2 |  |
| 3 |  |
| 4 |  |
| 5 |  |
| 6 |  |
| 7 |  |
| 8 |  |

TABLE 1-continued

| Substituent Number | A |
|---|---|
| 9 |  |
| 10 |  |
| 11 |  |
| 12 |  |
| 13 |  |
| 14 |  |
| 15 |  |
| 16 |  |
| 17 |  |
| 18 |  |
| 19 |  |
| 20 |  |
| 21 |  |
| 22 |  |
| 23 |  |
| 24 |  |

TABLE 1-continued
| Substituent Number | A |
|---|---|
| 25 | 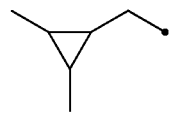 |
| 26 | 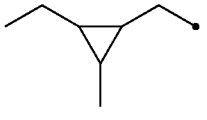 |
| 27 | 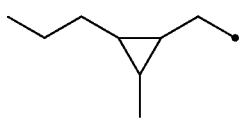 |
| 28 | 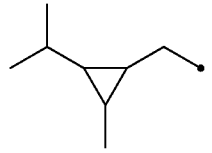 |
| 29 | 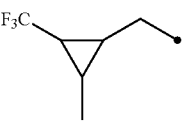 |
| 30 | 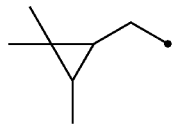 |
TABLE 2
| Substituent Number | A |
|---|---|
| 31 | 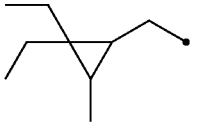 |
| 32 | 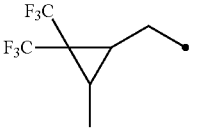 |
| 33 | 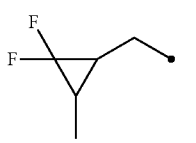 |
| 34 | 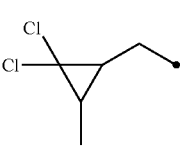 |
TABLE 2-continued
| Substituent Number | A |
|---|---|
| 35 | 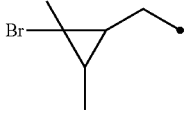 |
| 36 | 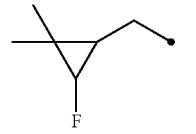 |
| 37 | 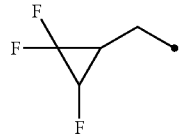 |
| 38 | 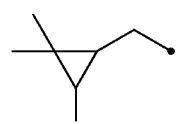 |
| 39 | 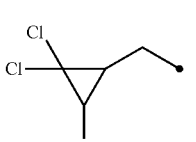 |
| 40 | 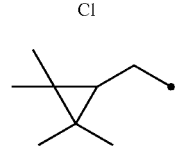 |
| 41 | 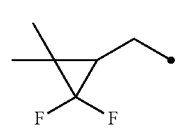 |
| 42 | 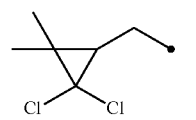 |
| 43 | 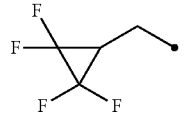 |
| 44 | 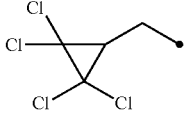 |
| 45 | 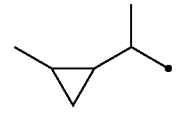 |

TABLE 2-continued

| Substituent Number | A |
|---|---|
| 46 | (ethyl-cyclopropyl with isopropyl) |
| 47 | (propyl-cyclopropyl with isopropyl) |
| 48 | (isopropyl-cyclopropyl with isopropyl) |
| 49 | (isobutyl-cyclopropyl with isopropyl) |
| 50 | (tert-butyl-cyclopropyl with isopropyl) |
| 51 | (neopentyl-cyclopropyl with isopropyl) |
| 52 | F₃C-cyclopropyl with isopropyl |
| 53 | F₃C-CH₂-cyclopropyl with isopropyl |
| 54 | F₃CF₂C-cyclopropyl with isopropyl |
| 55 | FCH₂-cyclopropyl with isopropyl |
| 56 | F-CH₂CH₂-cyclopropyl with isopropyl |
| 57 | ClCH₂-cyclopropyl with isopropyl |
| 58 | Cl-CH₂CH₂-cyclopropyl with isopropyl |
| 59 | F-cyclopropyl with isopropyl |
| 60 | Cl-cyclopropyl with isopropyl |

TABLE 3

| Substituent Number | A |
|---|---|
| 61 | Br-cyclopropyl with isopropyl |
| 62 | (dimethyl-cyclopropyl with isopropyl) |
| 63 | (diethyl-cyclopropyl with isopropyl) |
| 64 | (dipropyl-cyclopropyl with isopropyl) |
| 65 | F₃C, F₃C-cyclopropyl with isopropyl |
| 66 | F, F-cyclopropyl with isopropyl |
| 67 | Cl, Cl-cyclopropyl with isopropyl |
| 68 | Br, Br-cyclopropyl with isopropyl |

TABLE 3-continued
| Substituent Number | A |
|---|---|
| 69 | 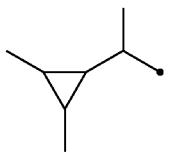 |
| 70 | 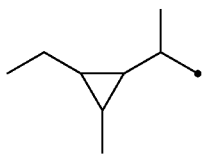 |
| 71 | 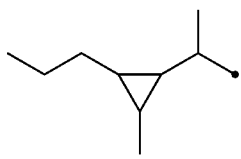 |
| 72 | 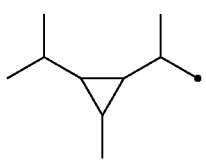 |
| 73 | 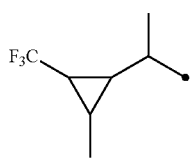 |
| 74 | 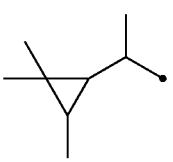 |
| 75 | 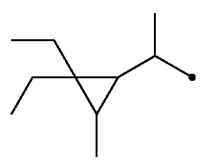 |
| 76 | 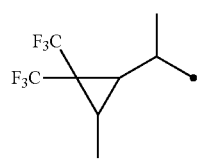 |
| 77 | 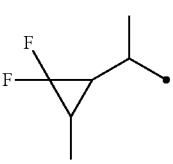 |
TABLE 3-continued
| Substituent Number | A |
|---|---|
| 78 | 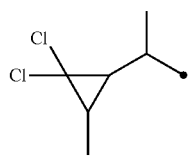 |
| 79 | 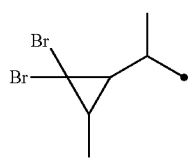 |
| 80 | 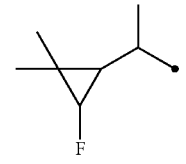 |
| 81 | 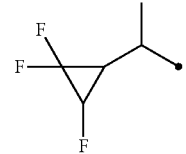 |
| 82 | 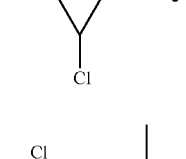 |
| 83 | 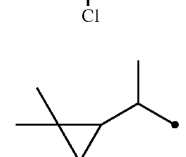 |
| 84 | 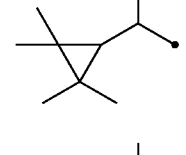 |
| 85 | 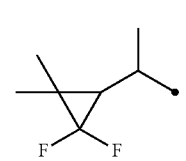 |
| 86 | 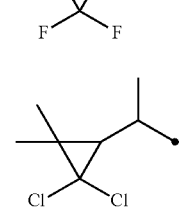 |

TABLE 3-continued
| Substituent Number | A |
|---|---|
| 87 | 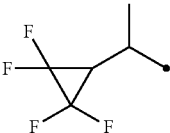 |
| 88 | 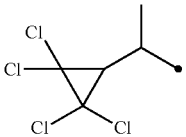 |
| 89 | 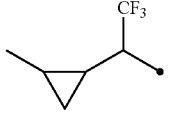 |
| 90 | 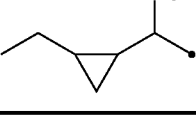 |
TABLE 4
| Substituent Number | A |
|---|---|
| 91 |  |
| 92 | 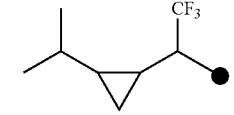 |
| 93 | 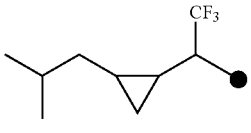 |
| 94 | 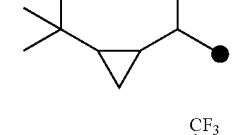 |
| 95 | 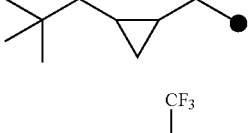 |
| 96 |  |
TABLE 4-continued
| Substituent Number | A |
|---|---|
| 97 | 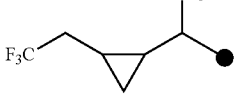 |
| 98 |  |
| 99 | 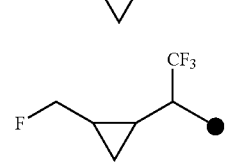 |
| 100 | 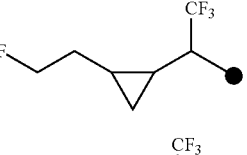 |
| 101 | 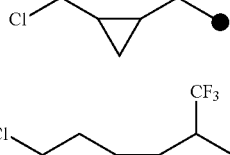 |
| 102 | 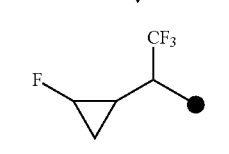 |
| 103 | 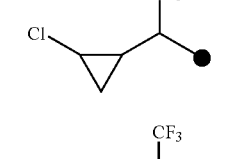 |
| 104 | 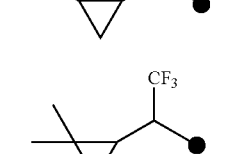 |
| 105 | 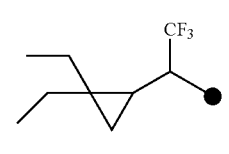 |
| 106 | 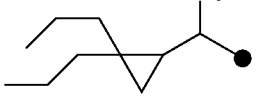 |
| 107 | 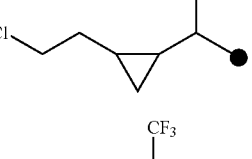 |
| 108 | 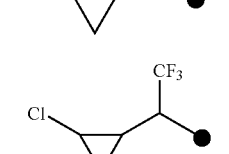 |

TABLE 4-continued

| Substituent Number | A |
|---|---|
| 109 | 1-(2,2-bis(trifluoromethyl)cyclopropyl)-2,2,2-trifluoroethyl |
| 110 | 1-(2,2-difluorocyclopropyl)-2,2,2-trifluoroethyl |
| 111 | 1-(2,2-dichlorocyclopropyl)-2,2,2-trifluoroethyl |
| 112 | 1-(2,2-dibromocyclopropyl)-2,2,2-trifluoroethyl |
| 113 | 1-(2,3-dimethylcyclopropyl)-2,2,2-trifluoroethyl |
| 114 | 1-(2-ethyl-3-methylcyclopropyl)-2,2,2-trifluoroethyl |
| 115 | 1-(3-methyl-2-propylcyclopropyl)-2,2,2-trifluoroethyl |
| 116 | 1-(2-isopropyl-3-methylcyclopropyl)-2,2,2-trifluoroethyl |
| 117 | 1-(3-methyl-2-(trifluoromethyl)cyclopropyl)-2,2,2-trifluoroethyl |
| 118 | 1-(2,2,3-trimethylcyclopropyl)-2,2,2-trifluoroethyl |

TABLE 4-continued

| Substituent Number | A |
|---|---|
| 119 | 1-(2,2-diethyl-3-methylcyclopropyl)-2,2,2-trifluoroethyl |
| 120 | 1-(2,2-bis(trifluoromethyl)-3-methylcyclopropyl)-2,2,2-trifluoroethyl |

TABLE 5

| Substituent Number | A |
|---|---|
| 121 | 1-(2,2-difluoro-3-methylcyclopropyl)-2,2,2-trifluoroethyl |
| 122 | 1-(2,2-dichloro-3-methylcyclopropyl)-2,2,2-trifluoroethyl |
| 123 | 1-(2,2-dibromo-3-methylcyclopropyl)-2,2,2-trifluoroethyl |
| 124 | 1-(3-fluoro-2,2-dimethylcyclopropyl)-2,2,2-trifluoroethyl |
| 125 | 1-(2,2,3-trifluorocyclopropyl)-2,2,2-trifluoroethyl |
| 126 | 1-(3-chloro-2,2-dimethylcyclopropyl)-2,2,2-trifluoroethyl |

TABLE 5-continued

| Substituent Number | A |
|---|---|
| 127 | |
| 128 | |
| 129 | |
| 130 | |
| 131 | |
| 132 | |
| 133 | |
| 134 | |
| 135 | |
| 136 | |
| 137 | |

TABLE 5-continued

| Substituent Number | A |
|---|---|
| 138 | |
| 139 | |
| 140 | |
| 141 | |
| 142 | |
| 143 | |
| 144 | |
| 145 | |
| 146 | |
| 147 | |
| 148 | |
| 149 | |
| 150 | |

TABLE 6

| Substituent Number | A |
|---|---|
| 151 | |
| 152 | |

TABLE 6-continued

| Substituent Number | A |
|---|---|
| 153 | (cyclopropane with two F3C groups, methyl, and CH2-●) |
| 154 | (cyclopropane with two F groups, methyl, and CH2-●) |
| 155 | (cyclopropane with two Cl groups, methyl, and CH2-●) |
| 156 | (cyclopropane with two Br groups, methyl, and CH2-●) |
| 157 | (cyclopropane with methyl groups and CH2-●) |
| 158 | (cyclopropane with ethyl and methyl groups and CH2-●) |
| 159 | (cyclopropane with propyl and methyl groups and CH2-●) |
| 160 | (cyclopropane with isopropyl and methyl groups and CH2-●) |
| 161 | (cyclopropane with F3C and methyl groups and CH2-●) |
| 162 | (cyclopropane with methyl groups and CH2-●) |
| 163 | (cyclopropane with substituents and CH2-●) |
| 164 | (cyclopropane with two F3C groups, methyl, and CH2-●) |

TABLE 6-continued

| Substituent Number | A |
|---|---|
| 165 | (cyclopropane with two F groups, methyl, and CH2-●) |
| 166 | (cyclopropane with two Cl groups, methyl, and CH2-●) |
| 167 | (cyclopropane with two Br groups, methyl, and CH2-●) |
| 168 | (cyclopropane with F substituent, methyl, and CH2-●) |
| 169 | (cyclopropane with two F groups, methyl, and CH2-●) |
| 170 | (cyclopropane with Cl substituent, methyl, and CH2-●) |
| 171 | (cyclopropane with three Cl groups, methyl, and CH2-●) |
| 172 | (cyclopropane with methyl groups and CH2-●) |
| 173 | (cyclopropane with two F groups, methyl, and CH2-●) |
| 174 | (cyclopropane with two Cl groups, methyl, and CH2-●) |
| 175 | (cyclopropane with four F groups, methyl, and CH2-●) |

TABLE 6-continued
| Substituent Number | A |
|---|---|
| 176 | 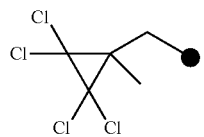 |
| 177 | 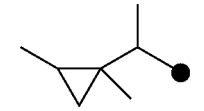 |
| 178 | 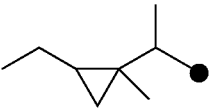 |
| 179 |  |
| 180 |  |
TABLE 7
| Substituent Number | A |
|---|---|
| 181 |  |
| 182 | 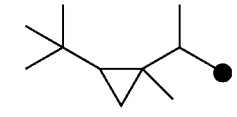 |
| 183 |  |
| 184 |  |
| 185 |  |
| 186 | 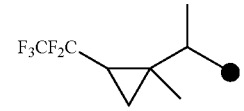 |
TABLE 7-continued
| Substituent Number | A |
|---|---|
| 187 |  |
| 188 | 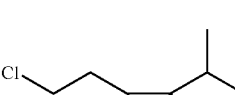 |
| 189 | 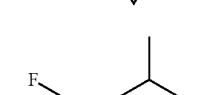 |
| 190 | 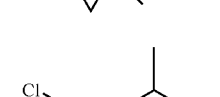 |
| 191 | 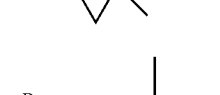 |
| 192 |  |
| 193 |  |
| 194 |  |
| 195 | 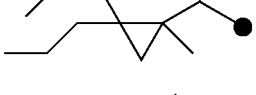 |
| 196 |  |
| 197 | 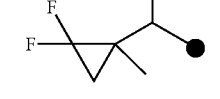 |
| 198 |  |

TABLE 7-continued

| Substituent Number | A |
|---|---|
| 199 | (cyclopropane with two Cl) |
| 200 | (cyclopropane with two Br) |
| 201 | (cyclopropane) |
| 202 | (cyclopropane with ethyl) |
| 203 | (cyclopropane with propyl) |
| 204 | (cyclopropane with isopropyl) |
| 205 | (cyclopropane with F₃C) |
| 206 | (cyclopropane) |
| 207 | (cyclopropane with two ethyl) |
| 208 | (cyclopropane with two F₃C) |

TABLE 7-continued

| Substituent Number | A |
|---|---|
| 209 | (cyclopropane with two F) |
| 210 | (cyclopropane with two Cl) |

TABLE 8

| Substituent Number | A |
|---|---|
| 211 | (cyclopropane with two Br) |
| 212 | (cyclopropane with F) |
| 213 | (cyclopropane with three F) |
| 214 | (cyclopropane with Cl) |
| 215 | (cyclopropane with three Cl) |
| 216 | (cyclopropane) |

TABLE 8-continued

| Substituent Number | A |
|---|---|
| 217 | (cyclopropane with gem-dimethyl, CF2 with two F, and CH(CH3)—● substituent) |
| 218 | (cyclopropane with gem-dimethyl, CCl2, and CH(CH3)—● substituent) |
| 219 | (cyclopropane with tetrafluoro substitution and CH(CH3)—● substituent) |
| 220 | (cyclopropane with tetrachloro substitution and CH(CH3)—● substituent) |
| 221 | (cyclopropane with methyl and CH(CF3)—● substituent) |
| 222 | (cyclopropane with ethyl, methyl and CH(CF3)—● substituent) |
| 223 | (cyclopropane with propyl and CH(CF3)—● substituent) |
| 224 | (cyclopropane with isopropyl, methyl and CH(CF3)—● substituent) |
| 225 | (cyclopropane with isobutyl, methyl and CH(CF3)—● substituent) |
| 226 | (cyclopropane with tert-butyl, methyl and CH(CF3)—● substituent) |

TABLE 8-continued

| Substituent Number | A |
|---|---|
| 227 | (cyclopropane with neopentyl, methyl and CH(CF3)—● substituent) |
| 228 | (cyclopropane with CF3, methyl and CH(CF3)—● substituent) |
| 229 | (cyclopropane with CF3CH2, methyl and CH(CF3)—● substituent) |
| 230 | (cyclopropane with F3CF2C, methyl and CH(CF3)—● substituent) |
| 231 | (cyclopropane with FCH2, methyl and CH(CF3)—● substituent) |
| 232 | (cyclopropane with FCH2CH2, methyl and CH(CF3)—● substituent) |
| 233 | (cyclopropane with ClCH2, methyl and CH(CF3)—● substituent) |
| 234 | (cyclopropane with ClCH2CH2, methyl and CH(CF3)—● substituent) |
| 235 | (cyclopropane with F, methyl and CH(CF3)—● substituent) |
| 236 | (cyclopropane with Cl, methyl and CH(CF3)—● substituent) |
| 237 | (cyclopropane with Br, methyl and CH(CF3)—● substituent) |
| 238 | (cyclopropane with gem-dimethyl, methyl and CH(CF3)—● substituent) |

TABLE 8-continued
| Substituent Number | A |
|---|---|
| 239 | 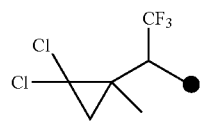 |
| 240 | 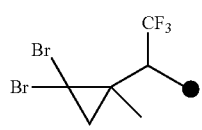 |
TABLE 9
| Substituent Number | A |
|---|---|
| 241 | 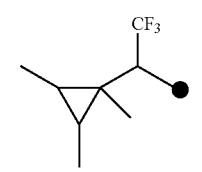 |
| 242 | 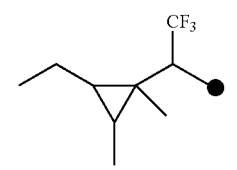 |
| 243 | 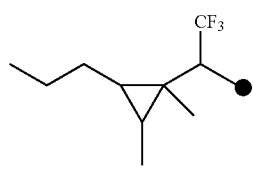 |
| 244 | 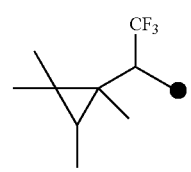 |
| 245 | 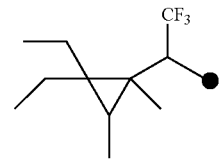 |
| 246 | 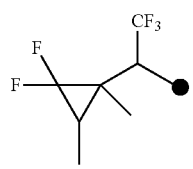 |
| 247 | 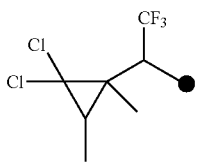 |
TABLE 9-continued
| Substituent Number | A |
|---|---|
| 248 | 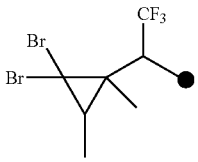 |
| 249 | 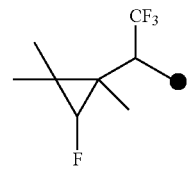 |
| 250 | 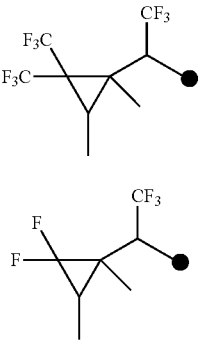 |
| 251 | |
| 252 | |
| 253 | |
| 254 | |
| 255 | |
| 256 | |

TABLE 9-continued

| Substituent Number | A |
|---|---|
| 257 | (cyclopropane with CF₃, F, F, F, methyl substituents) |
| 258 | (cyclopropane with CF₃, methyl groups, Cl substituent) |
| 259 | (cyclopropane with CF₃, Cl, Cl, Cl, methyl substituents) |
| 260 | (cyclopropane with CF₃ and methyl substituents) |
| 261 | (cyclopropane with CF₃, methyl groups, F, F substituents) |
| 262 | (cyclopropane with CF₃, methyl groups, Cl, Cl substituents) |
| 263 | (cyclopropane with CF₃, F, F, F, methyl substituents) |
| 264 | (cyclopropane with CF₃, Cl, Cl, Cl, Cl, methyl substituents) |
| 265 | (cyclopropane with CF₃ and methyl substituent) |
| 266 | (cyclopropane with CF₃ and ethyl substituent) |

TABLE 9-continued

| Substituent Number | A |
|---|---|
| 267 | (cyclopropane with CF₃ and propyl substituent) |
| 268 | (cyclopropane with CF₃ and isopropyl substituent) |
| 269 | (cyclopropane with CF₃ and isobutyl substituent) |
| 270 | (cyclopropane with CF₃ and tert-butyl substituent) |

TABLE 10

| Substituent Number | A |
|---|---|
| 271 | (cyclopropane with CF₃ and tert-butyl substituent) |
| 272 | (cyclopropane with CF₃ and F₃C substituents) |
| 273 | (cyclopropane with CF₃ and F₃C-CH₂ substituent) |
| 274 | (cyclopropane with CF₃ and F₃CF₂C substituent) |
| 275 | (cyclopropane with CF₃ and F-CH₂ substituent) |
| 276 | (cyclopropane with CF₃ and F-CH₂CH₂ substituent) |
| 277 | (cyclopropane with CF₃ and Cl-CH₂ substituent) |
| 278 | (cyclopropane with CF₃ and Cl-CH₂CH₂ substituent) |
| 279 | (cyclopropane with CF₃ and F substituent) |
| 280 | (cyclopropane with CF₃ and Cl substituent) |
| 281 | (cyclopropane with CF₃ and Br substituent) |

TABLE 10-continued
| Substituent Number | A |
|---|---|
| 282 |  |
| 283 | 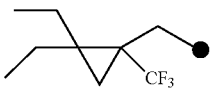 |
| 284 | 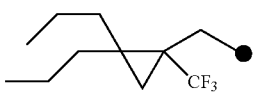 |
| 285 |  |
| 286 |  |
| 287 |  |
| 288 |  |
| 289 |  |
| 290 | 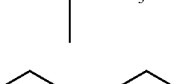 |
| 291 |  |
| 292 |  |
| 293 | 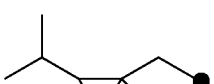 |
| 294 |  |
TABLE 10-continued
| Substituent Number | A |
|---|---|
| 295 |  |
| 296 |  |
| 297 |  |
| 298 |  |
| 299 |  |
| 300 |  |
TABLE 11
| Substituent Number | A |
|---|---|
| 301 |  |
| 302 |  |
| 303 | 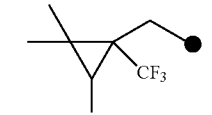 |

TABLE 11-continued

| Substituent Number | A |
|---|---|
| 304 | (structure: cyclopropane with gem-dimethyl, CF3, and CH2CH- attachment) |
| 305 | (structure: cyclopropane with dimethyl, two F, CF3, and CH2CH- attachment) |
| 306 | (structure: cyclopropane with methyl, two Cl, CF3, and CH2CH- attachment) |
| 307 | (structure: cyclopropane with four F, CF3, and CH2CH- attachment) |
| 308 | (structure: cyclopropane with four Cl, CF3, and CH2CH- attachment) |
| 309 | (structure: cyclopropane with methyl, CF3, and CH- attachment) |
| 310 | (structure: cyclopropane with ethyl, CF3, and CH- attachment) |
| 311 | (structure: cyclopropane with n-propyl, CF3, and CH- attachment) |
| 312 | (structure: cyclopropane with isopropyl, CF3, and CH- attachment) |
| 313 | (structure: cyclopropane with isobutyl, CF3, and CH- attachment) |
| 314 | (structure: cyclopropane with t-butyl, CF3, and CH- attachment) |

TABLE 11-continued

| Substituent Number | A |
|---|---|
| 315 | (structure: cyclopropane with neopentyl, CF3, and CH- attachment) |
| 316 | (structure: cyclopropane with CF3, CF3, and CH- attachment) |
| 317 | (structure: cyclopropane with CH2CF3, CF3, and CH- attachment) |
| 318 | (structure: cyclopropane with CH2CF2CF3, CF3, and CH- attachment) |
| 319 | (structure: cyclopropane with CH2F, CF3, and CH- attachment) |
| 320 | (structure: cyclopropane with CH2CH2F, CF3, and CH- attachment) |
| 321 | (structure: cyclopropane with CH2Cl, CF3, and CH- attachment) |
| 322 | (structure: cyclopropane with CH2CH2Cl, CF3, and CH- attachment) |
| 323 | (structure: cyclopropane with F, CF3, and CH- attachment) |
| 324 | (structure: cyclopropane with Cl, CF3, and CH- attachment) |
| 325 | (structure: cyclopropane with Br, CF3, and CH- attachment) |
| 326 | (structure: cyclopropane with gem-dimethyl, CF3, and CH- attachment) |

TABLE 11-continued

| Substituent Number | A |
|---|---|
| 327 | (cyclopropane with two ethyl groups, CF3) |
| 328 | (cyclopropane with propyl and butyl, CF3) |
| 329 | (cyclopropane with two F3C, CF3) |
| 330 | (cyclopropane with two F, CF3) |

TABLE 12

| Substituent Number | A |
|---|---|
| 331 | (cyclopropane with two Cl, CF3) |
| 332 | (cyclopropane with two Br, CF3) |
| 333 | (cyclopropane with methyl, CF3) |
| 334 | (cyclopropane with ethyl, methyl, CF3) |
| 335 | (cyclopropane with propyl, methyl, CF3) |
| 336 | (cyclopropane with isopropyl, methyl, CF3) |

TABLE 12-continued

| Substituent Number | A |
|---|---|
| 337 | (cyclopropane with F3C, CF3) |
| 338 | (cyclopropane with two methyl, CF3) |
| 339 | (cyclopropane with ethyl, methyl, CF3) |
| 340 | (cyclopropane with two F3C, methyl, CF3) |
| 341 | (cyclopropane with two F, methyl, CF3) |
| 342 | (cyclopropane with two Cl, methyl, CF3) |
| 343 | (cyclopropane with two Br, methyl, CF3) |
| 344 | (cyclopropane with methyl, CF3, F) |
| 345 | (cyclopropane with two F, CF3, F) |

TABLE 12-continued
| Substituent Number | A |
|---|---|
| 346 | 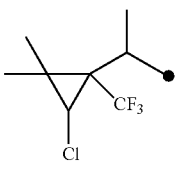 |
| 347 | 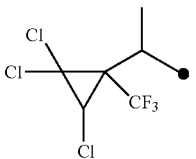 |
| 348 | 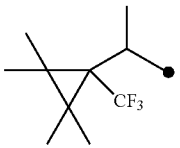 |
| 349 | 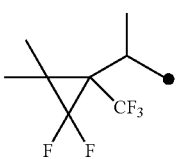 |
| 350 | 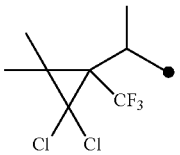 |
| 351 | 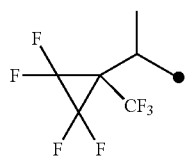 |
| 352 | 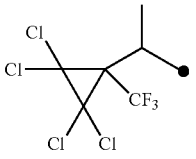 |
| 353 | 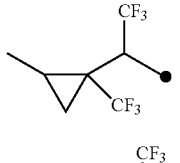 |
| 354 | 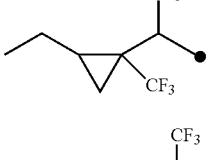 |
| 355 | 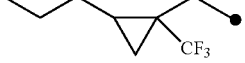 |
TABLE 12-continued
| Substituent Number | A |
|---|---|
| 356 | 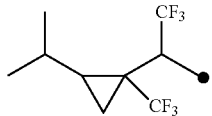 |
| 357 |  |
| 358 | 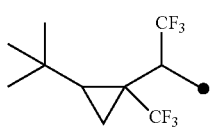 |
| 359 | 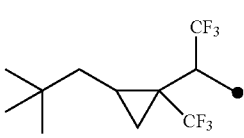 |
| 360 | 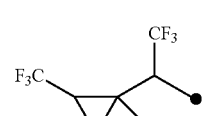 |
TABLE 13
| Substituent Number | A |
|---|---|
| 361 | 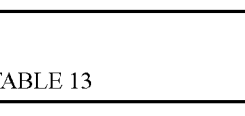 |
| 362 | 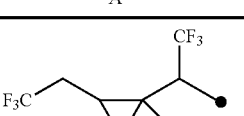 |
| 363 | 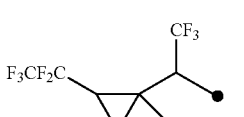 |
| 364 | 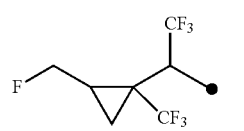 |
| 365 | 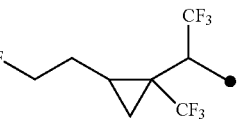 |

TABLE 13-continued

| Substituent Number | A |
|---|---|
| 366 | 2-chloroethyl, CF3, CF3 cyclopropyl |
| 367 | F, CF3, CF3 cyclopropyl |
| 368 | Cl, CF3, CF3 cyclopropyl |
| 369 | Br, CF3, CF3 cyclopropyl |
| 370 | dimethyl, CF3, CF3 cyclopropyl |
| 371 | diethyl, CF3, CF3 cyclopropyl |
| 372 | dipropyl, CF3, CF3 cyclopropyl |
| 373 | bis-CF3, CF3, CF3 cyclopropyl |
| 374 | F, F, CF3, CF3 cyclopropyl |
| 375 | Cl, Cl, CF3, CF3 cyclopropyl |
| 376 | Br, Br, CF3, CF3 cyclopropyl |
| 377 | dimethyl, CF3, CF3 cyclopropyl |
| 378 | ethyl, methyl, CF3, CF3 cyclopropyl |
| 379 | propyl, methyl, CF3, CF3 cyclopropyl |
| 380 | isopropyl, methyl, CF3, CF3 cyclopropyl |
| 381 | CF3, methyl, CF3, CF3 cyclopropyl |
| 382 | dimethyl, methyl, CF3, CF3 cyclopropyl |
| 383 | diethyl, methyl, CF3, CF3 cyclopropyl |
| 384 | bis-CF3, methyl, CF3, CF3 cyclopropyl |
| 385 | F, F, methyl, CF3, CF3 cyclopropyl |

TABLE 13-continued

| Substituent Number | A |
|---|---|
| 386 | cyclopropane with Cl, Cl, CH₃, CF₃, CH(CF₃)– |
| 387 | cyclopropane with Br, Br, CH₃, CF₃, CH(CF₃)– |
| 388 | cyclopropane with (CH₃)₂, F, CF₃, CH(CF₃)– |
| 389 | cyclopropane with F, F, F, CF₃, CH(CF₃)– |
| 390 | cyclopropane with (CH₃)₂, Cl, CF₃, CH(CF₃)– |

TABLE 14

| Substituent Number | A |
|---|---|
| 391 | cyclopropane with Cl, Cl, Cl, CF₃, CH(CF₃)– |
| 392 | cyclopropane with (CH₃)₂, (CH₃), CF₃, CH(CF₃)– |
| 393 | cyclopropane with (CH₃)₂, F, F, CF₃, CH(CF₃)– |

TABLE 14-continued

| Substituent Number | A |
|---|---|
| 394 | cyclopropane with (CH₃)₂, Cl, Cl, CF₃, CH(CF₃)– |
| 395 | cyclopropane with F, F, F, F, CF₃, CH(CF₃)– |
| 396 | cyclopropane with Cl, Cl, Cl, Cl, CF₃, CH(CF₃)– |
| 397 | cyclopropane with CH₃, Et, Et– |
| 398 | cyclopropane with Et, Et, Et– |
| 399 | cyclopropane with n-Pr, Et, Et– |
| 400 | cyclopropane with i-Pr, Et, Et– |
| 401 | cyclopropane with i-Bu, Et, Et– |
| 402 | cyclopropane with t-Bu, Et, Et– |
| 403 | cyclopropane with neopentyl, Et, Et– |
| 404 | cyclopropane with CF₃, Et, Et– |
| 405 | cyclopropane with CF₃CH₂, Et, Et– |
| 406 | cyclopropane with F₃CF₂C, Et, Et– |
| 407 | cyclopropane with FCH₂, Et, Et– |

TABLE 14-continued
| Substituent Number | A |
|---|---|
| 408 | 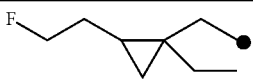 |
| 409 | 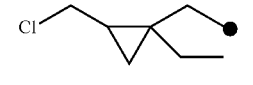 |
| 410 |  |
| 411 |  |
| 412 |  |
| 413 | 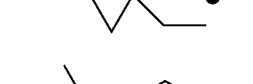 |
| 414 |  |
| 415 |  |
| 416 |  |
| 417 |  |
| 418 |  |
| 419 | 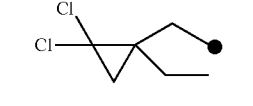 |
| 420 | 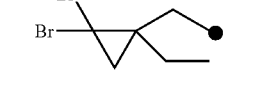 |
TABLE 15
| Substituent Number | A |
|---|---|
| 421 | 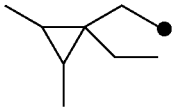 |
| 422 |  |
| 423 |  |
| 424 |  |
| 425 |  |
| 426 | 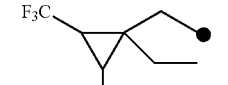 |
| 427 | 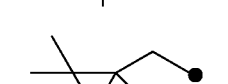 |
| 428 |  |
| 429 |  |
| 430 |  |
| 431 |  |
| 432 |  |

TABLE 15-continued

| Substituent Number | A |
|---|---|
| 433 | (cyclopropyl with F, F, F substituents) |
| 434 | (cyclopropyl with methyl, Cl) |
| 435 | (cyclopropyl with Cl, Cl, Cl) |
| 436 | (cyclopropyl with two methyls) |
| 437 | (cyclopropyl with two methyls, F, F) |
| 438 | (cyclopropyl with two methyls, Cl, Cl) |
| 439 | (cyclopropyl with two methyls, F, F, F) |
| 440 | (cyclopropyl with Cl, Cl, Cl, Cl) |
| 441 | (cyclopropyl with isopropyl) |
| 442 | (cyclopropyl with ethyl, isopropyl) |
| 443 | (cyclopropyl with n-propyl, isopropyl) |

TABLE 15-continued

| Substituent Number | A |
|---|---|
| 444 | (cyclopropyl with isopropyl, isopropyl) |
| 445 | (cyclopropyl with isobutyl, isopropyl) |
| 446 | (cyclopropyl with t-butyl, isopropyl) |
| 447 | (cyclopropyl with neopentyl, isopropyl) |
| 448 | (cyclopropyl with $F_3C$, isopropyl) |
| 449 | (cyclopropyl with $F_3C$-CH$_2$, isopropyl) |
| 450 | (cyclopropyl with $F_3CF_2C$, isopropyl) |

TABLE 16

| Substituent Number | A |
|---|---|
| 451 | (cyclopropyl with FCH$_2$, isopropyl) |
| 452 | (cyclopropyl with F-CH$_2$CH$_2$, isopropyl) |
| 453 | (cyclopropyl with ClCH$_2$, isopropyl) |
| 454 | (cyclopropyl with Cl-CH$_2$CH$_2$, isopropyl) |

TABLE 16-continued

| Substituent Number | A |
|---|---|
| 455 | |
| 456 | |
| 457 | |
| 458 | |
| 459 | |
| 460 | |
| 461 | |
| 462 | |
| 463 | |
| 464 | |
| 465 | |
| 466 | |
| 467 | |
| 468 | |
| 469 | |
| 470 | |
| 471 | |
| 472 | |
| 473 | |
| 474 | |
| 475 | |

TABLE 16-continued

| Substituent Number | A |
|---|---|
| 476 | |
| 477 | |
| 478 | |
| 479 | |
| 480 | |

TABLE 17

| Substituent Number | A |
|---|---|
| 481 | |
| 482 | |
| 483 | |

TABLE 17-continued

| Substituent Number | A |
|---|---|
| 484 | |
| 485 | |
| 486 | |
| 487 | |
| 488 | |
| 489 | |
| 490 | |
| 491 | |
| 492 | |
| 493 | |
| 494 | |

TABLE 17-continued

| Substituent Number | A |
|---|---|
| 495 | (structure) |
| 496 | (structure) |
| 497 | (structure) |
| 498 | (structure) |
| 499 | (structure) |
| 500 | (structure) |
| 501 | (structure) |
| 502 | (structure) |
| 503 | (structure) |
| 504 | (structure) |
| 505 | (structure) |
| 506 | (structure) |

TABLE 17-continued

| Substituent Number | A |
|---|---|
| 507 | (structure) |
| 508 | (structure) |
| 509 | (structure) |
| 510 | (structure) |

TABLE 18

| Substituent Number | A |
|---|---|
| 511 | (structure) |
| 512 | (structure) |
| 513 | (structure) |
| 514 | (structure) |

TABLE 18-continued

| Substituent Number | A |
|---|---|
| 515 | (structure with CF₃) |
| 516 | (structure with F₃C, F₃C, CF₃) |
| 517 | (structure with F, F, CF₃) |
| 518 | (structure with Cl, Cl, CF₃) |
| 519 | (structure with Br, Br, CF₃) |
| 520 | (structure with CF₃, F) |
| 521 | (structure with F, F, CF₃, F) |
| 522 | (structure with CF₃, Cl) |
| 523 | (structure with Cl, Cl, CF₃, Cl) |
| 524 | (structure with CF₃) |
| 525 | (structure with CF₃, F, F) |
| 526 | (structure with CF₃, Cl, Cl) |
| 527 | (structure with F, F, CF₃, F) |
| 528 | (structure with Cl, Cl, CF₃, Cl, Cl) |

Next, formulation examples will be shown. The part means part by weight.

Formulation Example 1

50 Parts of any one compound of Compounds of Present Invention (1-1) to (1-16), 3 parts of calcium lignosulfonate, 2 parts of magnesium lauryl sulfate and 45 parts of synthetic hydrous silicon oxide are well pulverized and mixed to obtain a formulation.

Formulation Example 2

20 Parts of any one compound of Compounds of Present Invention (1-1) to (1-16) and 1.5 parts of sorbitan trioleate are mixed with 28.5 parts of an aqueous solution containing 2 parts of polyvinyl alcohol, and the mixture is finely pulverized by a wet pulverizing method, then 40 parts of an aqueous solution containing 0.05 parts of xanthan gum and 0.1 parts of aluminum magnesium silicate is added thereto. 10 Parts of propylene glycol is further added, and the mixture is stirred and mixed to obtain a formulation.

Formulation Example 3

2 Parts of any one compound of Compounds of Present Invention (1-1) to (1-16), 88 parts of kaolin clay and 10 parts of talc are well pulverized and mixed to obtain a formulation.

Formulation Example 4

5 Parts of any one compound of Compounds of Present Invention (1-1) to (1-16), 14 parts of polyoxyethylenestyrylphenyl ether, 6 parts of calcium dodecylbenzenesulfonate and 75 parts of xylene are well mixed to obtain a formulation.

Formulation Example 5

2 Parts of any one compound of Compounds of Present Invention (1-1) to (1-16), 1 part of synthetic hydrous silicon oxide, 2 parts of calcium lignosulfonate, 30 parts of bentonite and 65 parts of kaolin clay are well pulverized and mixed, then water is added, and the mixture is well kneaded, granulated and dried to obtain a formulation.

Formulation Example 6

10 Parts of any one compound of Compounds of Present Invention (1-1) to (1-16); 35 parts of white carbon containing 50 parts of polyoxyethylene alkyl ether sulfate ammonium salt; and 55 parts of water are mixed and finely pulverized by a wet pulverization method to obtain a formulation.

Next, it will be shown by test examples that the compound of the present invention is useful in controlling plant diseases.

The control effect was evaluated by visually observing the area of lesions on a test plant on the investigation and comparing the area of lesions of a plant treated with the compound of the present invention with the area of lesions of a non-treated plant.

Test Example 1

A soil was filled into a plastic pot, and rice (variety: Nipponbare) was seeded therein, and grown in a greenhouse for 20 days. Thereafter, Compounds of Present Invention (1-1) and (1-16) were each formed into a formulation according to Formulation Example 2, and diluted with water so as to have a predetermined concentration (500 ppm), and then applied to foliage by spraying so that it was sufficiently adhered to the leaf surface of the rice. After spraying, the plants were air-dried, and the spray-treated rice and the rice seedling (variety: Nipponbare) affected by *Magnaporthe grisea* were left for 6 days while they were brought into contact with each other at 24° C. in the daytime and 20° C. at night under high humidity, and then the lesion area was investigated. As a result, the lesion area of the plants treated with either one of Compounds of Present Invention (1-1) and (1-16) was 30% or less of the lesion area in the non-treated plant.

Test Example 2

A soil was filled into a plastic pot, and wheat (variety: Shirogane) was seeded therein, and grown in a greenhouse for 9 days. Thereafter, spores of wheat *Puccinia recondita* were inoculated by sprinkling them on the wheat. The wheat was placed at 23° C. under darkness and high humidity for 1 day, and then air-dried. Compounds of Present Invention (1-1) and (1-16) were each formed into a formulation according to Formulation Example 2, then diluted with water so as to have a predetermined concentration (200 ppm), and applied to foliage by spraying so that it was sufficiently adhered to the leaf surface of the wheat. After spraying, the plants were air-dried and further left under illumination for 7 days, and then the lesion area was investigated. As a result, the lesion area of the plants treated with either one of Compounds of Present Invention (1-1) and (1-16) was 30% or less of the lesion area in the non-treated plant.

Test Example 3

A soil was filled into a plastic pot, and wheat (variety: Shirogane) was seeded therein, and grown in a greenhouse for 9 days. Compounds of Present Invention (1-2), (1-3) and (1-6) to (1-16) were each formed into a formulation according to Formulation Example 2, then diluted with water so as to have a predetermined concentration (200 ppm), and applied to foliage by spraying so that it was sufficiently adhered to the leaf surface of the wheat. After spraying, the plants were air-dried and grown under illumination at 18° C. for 5 days, and then spores of wheat *Puccinia recondita* were inoculated by sprinkling them on the wheat. After inoculating, the plants were placed at 23° C. under darkness and high humidity for 1 day, then grown under illumination at 18° C. for 8 days, and the lesion area was investigated. As a result, the lesion area of the plants treated with any one of Compounds of Present Invention (1-2), (1-3) and (1-6) to (1-16) was 30% or less of the lesion area in the non-treated plant.

Test Example 4

A soil was filled into a plastic pot, and cucumber (variety: Sagamihanjiro) was seeded therein, and grown in a greenhouse for 12 days. Compounds of Present Invention 1, 2 and 16 were each formed into a formulation according to Formulation Example 2, then diluted with water so as to have a predetermined concentration (200 ppm), and applied to foliage by spraying so that it was sufficiently adhered to the leaf surface of the cucumber. After spraying, the plants were air-dried, and spores of cucumber *Sphaerotheca fuliginea* were inoculated by sprinkling them. The plants were grown in a greenhouse at 24° C. in the daytime and 20° C. at night for 11 days, and then the lesion area was investigated. As a result, the lesion area of the plants treated with any one of Compounds of Present Invention (1-1), (1-2) and (1-16) was 30% or less of the lesion area in the non-treated plant.

Test Example 5

A soil was filled into a plastic pot, and wheat (variety: Apogee) was seeded therein, and grown in a greenhouse for 10 days. Compounds of Present Invention (1-8), (1-11), (1-12), (1-14) and (1-15) were each formed into a formulation according to Formulation Example 2, then diluted with water so as to have a predetermined concentration (200 ppm), and applied to foliage by spraying so that it was sufficiently adhered to the leaf surface of the wheat. After spraying, the plants were air-dried, and after 4 days, an aqueous suspension of spores of wheat *Septoria tritici* was inoculated by spraying it. After inoculating, the plants were placed at 18° C. under high humidity for 3 days and subsequently placed under illumination for 14 to 18 days, and then the lesion area was investigated. As a result, the lesion area of the plants treated with any one of Compounds of Present Invention (1-8), (1-11), (1-12), (1-14) and (1-15) was 30% or less of the lesion area in the non-treated plant.

Test Example 6

A soil was filled into a plastic pot, and barley (variety: Nishinohoshi) was seeded therein, and grown in a greenhouse for 7 days. Compounds of Present Invention (1-12), (1-14) and (1-16) were each formed into a formulation according to Formulation Example 2, then diluted with water so as to have a predetermined concentration (200 ppm), and applied to foliage by spraying so that it was sufficiently adhered to the leaf surface of the barley. After spraying, the plants were air-dried, and after 2 days, an aqueous suspension of spores of barley *Pyrenophora teres* was inoculated by spraying it. After inoculating, the plants were placed in a greenhouse at 23° C. in the daytime and 20° C. at night under high humidity for 3 days, and subsequently grown in a greenhouse for 7 days, and then the lesion area was investigated. As a result, the lesion area of the plants treated with any one of Compounds of Present Invention (1-12), (1-14) and (1-16) was 30% or less of the lesion area in the non-treated plant.

Test Example 7

A soil was filled into a plastic pot, and barley (variety: Mikamo Golden) was seeded therein, and grown in a greenhouse for 7 days. Compounds of Present Invention (1-8), (1-12) and (1-14) to (1-16) were each formed into a formulation according to Formulation Example 2, then diluted with water so as to have a predetermined concentration (200 ppm), and applied to foliage by spraying so that it was sufficiently adhered to the leaf surface of the barley. After spraying, the plants were air-dried, and after 2 days, an aqueous suspension of spores of barley *Rhynchosporium secalis* was inoculated by spraying it. After inoculating, the plants were placed in a greenhouse at 23° C. in the daytime and 20° C. at night under high humidity for 3 days, and subsequently grown in a greenhouse for 7 days, and then the lesion area was investigated. As a result, the lesion area of the plants treated with any one of Compounds of Present Invention (1-8), (1-12) and (1-14) to (1-16) was 30% or less of the lesion area in the non-treated plant.

Test Example 8

A soil was filled into a plastic pot, and soybean (variety: Kurosengoku) was seeded therein, and grown in a greenhouse for 13 days. Compounds of Present Invention (1-1) to (1-3) and (1-5) to (1-15) were each formed into a formulation according to Formulation Example 2, then diluted with water so as to have a predetermined concentration (200 ppm), and applied to foliage by spraying so that it was sufficiently adhered to the leaf surface of the soybean. After spraying, the plants were air-dried, and after 2 days, an aqueous suspension of spores of soybean *Phakopsora pachyrhizi* was inoculated by spraying it. After inoculating, the plants were placed in a greenhouse at 23° C. in the daytime and 20° C. at night under high humidity for 3 days, and subsequently grown in a greenhouse for 14 days, and then the lesion area was investigated. As a result, the lesion area of the plants treated with any one of Compounds of Present Invention (1-1) to (1-3) and (1-5) to (1-15) was 30% or less of the lesion area in the non-treated plant.

Test Example 9

A soil was filled into a plastic pot, and soybean (variety: Kurosengoku) was seeded therein, and grown in a greenhouse for 13 days. Thereafter, an aqueous suspension of spores of soybean *Phakopsora pachyrhizi* was inoculated by spraying it on the soybean. The soybean was placed at 23° C. under high humidity for 1 day, and then air-dried. Compounds of Present Invention (1-1) to (1-15) were each formed into a formulation according to Formulation Example 2, then diluted with water so as to have a predetermined concentration (200 ppm), and applied to foliage by spraying so that it was sufficiently adhered to the leaf surface of the soybean. After spraying, the plants were air-dried, and further left under illumination for 14 days, and then the lesion area was investigated. As a result, the lesion area of the plants treated with any one of Compounds of Present Invention (1-1) to (1-15) was 30% or less of the lesion area in the non-treated plant.

Comparative Test Example

A soil was filled into a plastic pot, and rice (variety: Nipponbare) was seeded therein, and grown in a greenhouse for 20 days. Thereafter, Compound of Present Invention (1-17) and Compound 267 (N'-(4-cyclohexylmethoxy-2,5-dimethylphenyl)-N,N-dimethylformamidine) described in WO2000/46184 were each formed into a formulation according to Formulation Example 2, and diluted with water so as to have a predetermined concentration (200 ppm), and then applied to foliage by spraying so that it was sufficiently adhered to the leaf surface of the rice. After spraying, the plants were air-dried, and the spray-treated rice and the rice seedling (variety: Nipponbare) affected by *Magnaporthe grisea* were left for 6 days while they were brought into contact with each other at 24° C. in the daytime and 20° C. at night under high humidity, and then the lesion area was investigated. As a result, as shown in Table A, in the same conditions, the lesion area of the plants treated with Compound of Present Invention (1-17) was 10% or less of the lesion area in the non-treated plant, and on the other hand, the lesion area of the plants treated with Compound 267 described in WO2000/46184 was 50% or less of the lesion area in the non-treated plant.

TABLE 19

| Compound | Concentration (ppm) | Lesion Area (%) |
|---|---|---|
| Compound of Present Invention (1-17) | 200 | 1-10 |
| Compound 267 in WO2000/46184 | 200 | 31-50 |

The results show that the compound of the present invention exhibits more excellent biological activity, as compared to the compound that has the closest structure among the compounds described in WO2000/46184.

The invention claimed is:
1. An amidine compound represented by formula (1)

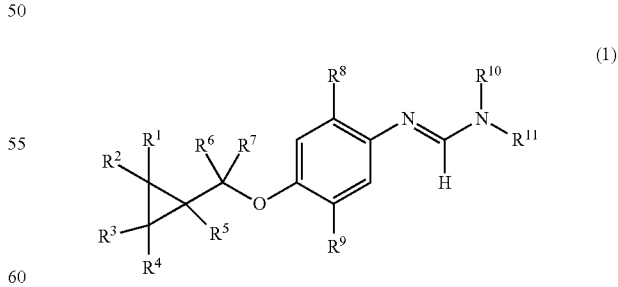

wherein $R^1$, $R^2$, $R^3$, $R^4$ and $R^5$ each independently represent a C1 to C5 alkyl group optionally having one or more halogen atoms, a hydrogen atom or a halogen atom;
  $R^6$ and $R^7$ each independently represent a hydrogen atom or a C1 to C3 alkyl group optionally having one or more halogen atoms;

$R^8$ and $R^9$ each independently represent a C1 to C3 alkyl group optionally having one or more halogen atoms, a C1 to C2 alkoxy group optionally having one or more halogen atoms or a halogen atom; and $R^{10}$ and $R^{11}$ each independently represent a C1 to C6 alkyl group optionally having one or more halogen atoms or a C2 to C6 alkenyl group optionally having one or more halogen atoms.

2. The amidine compound according to claim 1, wherein $R^8$ and $R^9$ are each independently a methyl group optionally having one or more halogen atoms;

$R^{10}$ is a methyl group; and $R^{11}$ is a C1 to C3 alkyl group or a C2 to C3 alkenyl group.

3. The amidine compound according to claim 1, wherein $R^1$, $R^2$, $R^3$, $R^4$ and $R^5$ are each independently a C1 to C5 alkyl group, a hydrogen atom or a halogen atom;

$R^8$, $R^9$ and $R^{10}$ are a methyl group; and $R^{11}$ is an ethyl group, a propyl group or a 2-propenyl group.

4. A plant disease controlling agent comprising the amidine compound as defined in claim 1.

5. A method for controlling plant diseases comprising applying an effective amount of the amidine compound as defined in claim 1 to a plant or soil.

\* \* \* \* \*